US012799505B2

(12) United States Patent
Yacoby et al.

(10) Patent No.: US 12,799,505 B2
(45) Date of Patent: Nov. 17, 2026

(54) PHOTOSYNTHETIC MICROALGAE AND USE THEREOF FOR HYDROGEN PRODUCTION

(71) Applicants: RAMOT AT TEL-AVIV UNIVERSITY LTD., Tel Aviv (IL); WESTFÄLISCHE WILHELMS-UNIVERSITÄT MÜNSTER, Münster (DE)

(72) Inventors: Iftach Yacoby, Tel Aviv (IL); Tamar Elman, Tel Aviv (IL); Oren Ben Zvi, Tel Aviv (IL); Chris Philip Schwier, Munster (DE); Thi Thu Hoai Ho, Munster (DE); Michael Hippler, Munster (DE)

(73) Assignees: RAMOT AL TEL-AVIV UNIVERSITY LTD., Tel Aviv (IL); WESTFAELISCHE WILHELMS-UNIVERSITAET MUENSTER, Muenster (DE)

( * ) Notice: Subject to any disclaimer, the term of this patent is extended or adjusted under 35 U.S.C. 154(b) by 597 days.

(21) Appl. No.: 18/250,594

(22) PCT Filed: Oct. 28, 2021

(86) PCT No.: PCT/IL2021/051282

§ 371 (c)(1),
(2) Date: Apr. 26, 2023

(87) PCT Pub. No.: WO2022/091101

PCT Pub. Date: May 5, 2022

(65) Prior Publication Data

US 2025/0043234 A1 Feb. 6, 2025

Related U.S. Application Data

(60) Provisional application No. 63/225,575, filed on Jul. 26, 2021, provisional application No. 63/106,923, filed on Oct. 29, 2020.

(51) Int. Cl.

*C12P 3/00* (2006.01)
*C12N 1/125* (2026.01)
*C12N 9/02* (2006.01)
*C12R 1/89* (2006.01)

(52) U.S. Cl.

CPC ................ *C12P 3/00* (2013.01); *C12N 1/125* (2021.05); *C12N 9/0067* (2013.01); *C12N 2510/02* (2013.01); *C12N 2511/00* (2013.01); *C12R 2001/89* (2021.05)

(58) Field of Classification Search

CPC .. C12N 1/125; C12N 9/0067; C12N 2510/02; C12N 2511/00; C12N 15/8269; C12N 1/12; C12P 3/00; C12R 2001/89

See application file for complete search history.

(56) References Cited

U.S. PATENT DOCUMENTS

| | | | | |
|---|---|---|---|---|
| 8,124,347 B2 | 2/2012 | Plummer | | |
| 8,663,958 B2 | 3/2014 | King | | |
| 8,759,058 B2 | 6/2014 | Plummer | | |
| 2007/0269874 A1* | 11/2007 | Kosourov | ................ | C12P 3/00 435/168 |
| 2009/0221052 A1 | 9/2009 | Hankamer | | |

OTHER PUBLICATIONS

Chen, M et al. Loss of algal proton gradient regulation 5 increases reactive oxygen species scavenging and H2 evolution. Journal of Integrative Plant Biology. 2016. 58: 943-946. Including Supporting Information. (Year: 2016).*

Batyrova, K. et al. Hydrogen production by a Chlamydomonas reinhardtii strain with inducible expression of Photosystem II. International Journal of Molecular Sciences. 2017. 18: 647. 14 pages. (Year: 2017).*

Merchant, SS et al. The Chlamydomonas genome reveals the evolution of key animal and plant functions. Science. 2007. 318: 245-251. (Year: 2007).*

Result 1 of SEQ ID No. 3 search performed on UniProt database. Sequence integrated into UniProtKB/TrEMBL on Dec. 4, 2007. Search performed on Mar. 30, 2026. (Year: 2007).*

Melis, A et al. Hydrogen production. Green algae as a source of energy. Plant Physiology. 2001. 127: 740-748. (Year: 2001).*

Bailleul et al., (2010) Electrochromism: a useful probe to study algal photosynthesis. Photosynth Res 106(1-2): 179-189. With erratum.

Ben-Zvi et al., (2019) Re-routing photosynthetic energy for continuous hydrogen production in vivo. Biotechnol Biofuels 12: 266.

Burlacot A (2019) The role of flavodiiron proteins during photosynthesis in the green microalga *Chlamydomonas reinhardtii* (Doctoral dissertation, Aix-Marseille, France). Dec. 31, 2019. 224 pages.

Dent et al., (2005) Functional genomics of eukaryotic photosynthesis using insertional mutagenesis of Chlamydomonas reinhardtii. Plant Physiol 137(2): 545-556.

Drop BA (2014) From Photosystem I to Photosystem II. PhD thesis, University of Groningen, Poland Dec. 31, 2014. 148 pages.

Eilenberg et al., (2016) The dual effect of a ferredoxin-hydrogenase fusion protein in vivo: successful divergence of the photosynthetic electron flux towards hydrogen production and elevated oxygen tolerance. Biotechnol Biofuels 9(1): 182.

Elman et al., (2022) Enhanced chloroplast-mitochondria crosstalk promotes ambient algal-H2 production. Cell Reports Physical Science 3(4): 100828.

Ganeteg et al., (2001) The properties of the chlorophyll a/b-binding proteins Lhca2 and Lhca3 studied in vivo using antisense inhibition. Plant Physiol 127(1): 150-158.

(Continued)

*Primary Examiner* — David W Berke-Schlessel
*Assistant Examiner* — Susan E. Fernandez
(74) *Attorney, Agent, or Firm* — Ballard Spahr LLP

(57) ABSTRACT

The present invention is in the field of molecular hydrogen ($H_2$) bio-production, particularly, the present invention provides genetically modified photosynthetic microalgae producing hydrogen in complete growth medium under ambient, continuous growth conditions at cost-effective amounts and to a process for hydrogen production using genetically modified photosynthetic microalga.

5 Claims, 17 Drawing Sheets

Specification includes a Sequence Listing.

(56) References Cited

OTHER PUBLICATIONS

Henikoff and Henikoff (1992) Amino acid substitution matrices from protein blocks. Proc Natl Acad Sci U S A 89(22): 10915-10919.

Jeffrey and Humphrey (1975) New spectrophotometric equations for determining chlorophylls a, b, c1 and c2 in higher plants, algae and natural phytoplankton. Biochemie und Physiologie der Pflanzen 167(2): 191-194.

Johnson et al., (2014) Proton gradient regulation 5-mediated cyclic electron flow under ATP- or redox-limited conditions: a study of ΔATpase pgr5 and ΔrbcL pgr5 mutants in the green alga *Chlamydomonas reinhardtii.* Plant Physiol 165(1): 438-452.

Joliot and Joliot (2002) Cyclic electron transfer in plant leaf. Proc Natl Acad Sci U S A 99(15): 10209-10214.

Khosravitabar and Hippler (2019) A new approach for improving microalgal biohydrogen photoproduction based on safe & fast oxygen consumption. International Journal of Hydrogen Energy 44(33): 17835-17844.

Kosourov et al., (2018) A new approach for sustained and efficient H2 photoproduction by Chlamydomonas reinhardtii. Energy Environ Sci 11: 1431-1436.

Li et al., (2016) An Indexed, Mapped Mutant Library Enables Reverse Genetics Studies of Biological Processes in Chlamydomonas reinhardtii. Plant Cell 28(2): 367-387.

Liran et al., (2016) Microoxic Niches within the Thylakoid Stroma of Air-Grown Chlamydomonas reinhardtii Protect [FeFe]-Hydrogenase and Support Hydrogen Production under Fully Aerobic Environment. Plant Physiol 172(1): 264-271.

Melis et al., (2000) Sustained photobiological hydrogen gas production upon reversible inactivation of oxygen evolution in the green alga *Chlamydomonas reinhardtii.* Plant Physiol 122(1): 127-136.

Milrad et al., (2018) Green Algal Hydrogenase Activity Is Outcompeted by Carbon Fixation before Inactivation by Oxygen Takes Place. Plant Physiol 177(3): 918-926.

Nagy et al., (2018) Water-splitting-based, sustainable and efficient H2 production in green algae as achieved by substrate limitation of the Calvin-Benson-Bassham cycle. Biotechnol Biofuels 11: 69.

Naschberger et al., (2021) Chloroplast photosystem I dimer and high resolution model of the complex with plastocyanin. bioRxiv preprint doi: https://doi.org/10.1101/2021.08.30.458224; this version posted Aug. 31, 2021. 37 pages.

Naumann et al., (2005) N-terminal processing of Lhca3 Is a key step in remodeling of the photosystem l-light-harvesting complex under iron deficiency in Chlamydomonas reinhardtii. J Biol Chem 280(21): 20431-20441.

Nawrocki et al., (2019) Maximal cyclic electron flow rate is independent of PGRL1 in Chlamydomonas. Biochim Biophys Acta Bioenerg 1860(5): 425-432.

Steinbeck et al., (2015) Deletion of Proton Gradient Regulation 5 (PGR5) and PGR5-Like 1 (PGRL1) proteins promote sustainable light-driven hydrogen production in Chlamydomonas reinhardtii due to increased PSII activity under sulfur deprivation. Front Plant Sci 6: 892.

Steinbeck et al., (2018) Structure of a PSI-LHCI-cyt b6f supercomplex in Chlamydomonas reinhardtii promoting cyclic electron flow under anaerobic conditions. Proc Natl Acad Sci U S A 115(41): 10517-10522.

Torzillo et al., (2015) Advances in the biotechnology of hydrogen production with the microalga *Chlamydomonas reinhardtii.* Crit Rev Biotechnol 35(4): 485-496.

Toth and Yacoby (2019) Paradigm Shift in Algal H2 Production: Bypassing Competitive Processes. Trends in Biotechnology 37(11): 1159-1163.

Tran et al., (2012) Intragenic enhancers and suppressors of phytoene desaturase mutations in Chlamydomonas reinhardtii. PLoS One 7(8): e42196.

Ho et al., (2022) Photosystem I light-harvesting proteins regulate photosynthetic electron transfer and hydrogen production. Plant Physiol 189(1): 329-343.

* cited by examiner

PHOTOSYNTHETIC MICROALGAE AND USE THEREOF FOR HYDROGEN PRODUCTION

The Sequence Listing in ASCII text file format of 5,581 bytes in size, created on Apr. 26, 2023, with the file name "2023-04-26SeqLst-YACOBY2," filed in the U.S. Patent and Trademark Office on even date herewith, is hereby incorporated herein by reference.

FIELD OF THE INVENTION

The present invention is in the field of molecular hydrogen ($H_2$) production. Particularly, the present invention relates to genetically modified photosynthetic microalgae producing hydrogen in complete medium under ambient, continuous growth conditions at cost-effective amounts, and to a process for hydrogen production using genetically modified photosynthetic microalgae.

BACKGROUND OF THE INVENTION

Molecular hydrogen ($H_2$) is a promising clean energy vector and carrier and a valuable commodity with over 60 million tons produced globally and used in many industrial technologies (e.g., fertilizer synthesis, petroleum refining). The current industrial method (over 95%) to produce hydrogen is steam reformation of natural gas, which produces carbon dioxide (and other pollutants) while consuming methane, a high-value fuel. Current technologies to produce hydrogen by reduction of protons are based on catalysts that use purified water, rare elements and/or have short lifespans. In contrast, hydrogen production by photosynthetic microbes ("photobiological $H_2$ [Bio$H_2$] production") represents an alternate strategy that makes use of sunlight and abundant resources (e.g., uncultivated soil, wastewater or seawater) and avoids competition with agriculture. Moreover, biological replication allows rapid and cheap production of solar bio-factories making $H_2$.

For cost effective industrial manufacturing, algal hydrogen production must be increased by about 5-fold. Two major challenges limit efficient biological $H_2$ production: inactivation of the hydrogen production catalyst (the hydrogenase enzyme) by molecular oxygen ($O_2$), which is a byproduct of photosynthesis; and limited electron flow from the photosynthetic apparatus to the hydrogenase.

Attempts to overcome inactivation of the hydrogenase enzyme suggested modifying the enzyme and/or the environmental conditions. For example, U.S. Pat. Nos. 8,124,347 and 8,759,058 disclose method for producing bacteria and green alga, particularly *Chlamydomonas reinhardtii*, that can produce hydrogen in quantities that exceed four hundred percent of the hydrogen produced by green alga in nature, by expressing in the alga a mutated or a chimeric hydrogenase. U.S. Pat. No. 8,663,958 discloses oxygen-resistant iron-hydrogenases ([Fe]-hydrogenases) for use in the production of hydrogen, host cells comprising same and use of the transformed, oxygen insensitive host cells in the bulk production of hydrogen in a light catalyzed reaction having water as the reactant.

Alternatively, anoxia in established by sulfur deprivation, which results in substantial degradation of the photosynthetic apparatus, including photosystem II (PSII). Under these conditions, the hydrogenase enzyme HydA becomes highly expressed and $H_2$ photoproduction is initiated, lasting for a few days (Melis, A., et al., 2000. Plant Physiol 122, 127-136; Nagy, V. et al., 2018. Biotechnol Biofuels 11, 69, doi:10.1186/s13068-018-1069-0). This approach is the currently most frequently used approached. However, due to degradation of PSII, the light to $H_2$ conversion efficiency is low.

Recently, a paradigm shift occurred in inducing $H_2$ production by green algae: instead of downregulating PSII activity, the newly developed $H_2$ production methods aim at maintaining the Calvin cycle (Calvin-Benson-Bassham [CBB]) inactive during $H_2$ production, as to direct the electrons delivered by the photosynthetic electron transport chain to $H_2$ production, at a high efficacy (Toth, S. Z. & Yacoby, I. 2019. Trends Biotechnol, doi:10.1016/j.tibtech.2019.05.001). This goal may be achieved by substrate limitation of the Calvin cycle and using continuous and strong light and reaching high $H_2$ production yields. Another proposed method applied light pulses in which $H_2$ production occurs with high light-to-$H_2$ conversion efficiency, without activating the Calvin cycle, supporting $H_2$ production (Nagy et al., 208, ibid; Kosourov, S., et al., 2018. Energy Environ. Sci. 1, 1431-1436). For long-term $H_2$ production, it is essential to maintain a low $O_2$ concentration level to minimize its inhibitory effect on the enzyme [FeFe]-hydrogenase (HydA); this can be achieved by employing an iron-salt based $O_2$ absorbent in the headspace or adding a mixture of ascorbate and copper to the alga culture (Khosravitabar, F. & Hippler, M. 2019. International Journal of Hydrogen Energy 44, 17835-17844, doi: 10.1016/j.ijhydene.2019.05.038).

U.S. Application Publication No. 2009/0221052 discloses a process for the production of hydrogen by a photosynthetic microorganism having electron transfer capability through a photosynthetic "light" reaction pathway and through a respiratory electron transfer chain involving an oxidative phosphorylation pathway, and which expresses a hydrogenase, in which the regulation of the oxidative phosphorylation pathway is disrupted with the result that electron flow along the respiratory electron transfer chain toward cytochrome oxidase (complex IV) is reduced, and culturing the microorganism under microoxic and illuminated conditions for hydrogen production. The oxidative phosphorylation is particularly disrupted through modulation of the activity of the mitochondrial transcription factor Moc1.

However, none of the hitherto described procedures were scaled up above 100 ml and, furthermore, are not likely being suitable for further scaling up. The most potent procedure to produce $H_2$ in green algae is the combination of genetic engineering to improve $H_2$ production and the application of sulfur deprivation.

There is a great need for and would be highly advantageous to have a bioprocess for $H_2$ production which is scalable and cost effective.

SUMMARY OF THE INVENTION

The present invention answers the above-described needs, providing photosynthetic microalgae that have been genetically modified to enable molecular hydrogen ($H_2$) production under conditions providing for cost-effective commercial production of hydrogen. Particularly, the present invention provides a double-mutant photosynthetic microalgae having a reduced expression and/or activity of Light Harvesting Complex Protein 2 (LHCA2) and Proton Gradient Regulation 5 (PGR5) protein, which can produce high hydrogen quantities under ambient air and light conditions for a period of days, particularly for between 5-20 days under temperatures up to about 35° C.-36° C. and light intensity enabling photosynthesis. According to certain embodiments, the photosynthetic microalgae is *Chlamydomonas reinhardtii*, and the double mutant microalga is named *Chlamydomonas* Elsa. The present invention further provides a scalable process for the photobiological production of hydrogen using the double-mutant photosynthetic microalgae of the invention as well as single mutant photosynthetic microalgae having a reduced expression and/or activity of PGR5.

The present invention is based in part on the unexpected finding that a pgr5 single mutant, and to a significantly higher extent a pgr5/lhca2 double-mutant *C. reinhardtii* produced high amounts of $H_2$ when exposed to continuous light after a short (couple of hours) dark period. Without wishing to be bound by any specific theory or mechanism of action, reducing PGR5 expression and/or activity results in ATP shortage within the microalga chloroplast, leading to high respiration rate in the mitochondria and formation of internal anoxia conditions favorable for hydrogenase activity, and reducing the $CO_2$ fixation via the Calvin cycle, thus paving the way to $H_2$ production. The electron flow towards $H_2$ production is further enhanced as a result of unbinding the LHCA2 to enable the formation and stabilization of photosystem I (PSI) super-complexes, such as the cytochrome $b_6f$ and ferredoxin-NADP+ reductase (FNR) (PSI-Cyt$b_6$f-FNR) super-complex and/or the formation of a PSI-dimeric structure, resulting in the overall hitherto non-achievable hydrogen production rate under ambient air and light conditions.

According to certain aspects, the present invention provides a genetically modified photosynthetic microalga having reduced expression and/or activity of Proton Gradient Regulation 5 (PGR5) protein and of Light Harvesting Complex Protein 2 (LHCA2) compared to the expression and/or activity of PGR5 and LHCA2 in a corresponding unmodified photosynthetic microalga.

According to certain embodiments, the genetically modified photosynthetic microalga is capable of producing elevated amount of hydrogen ($H_2$) compared to the $H_2$ amount produced by the corresponding unmodified photosynthetic microalga when subjected to the same growth conditions.

According to certain embodiments, the genetically modified photosynthetic microalga is capable of producing a cumulative amount of hundreds of milliliters of $H_2$ per 1 Liter culture comprising microalgae at a density of 10 mg chlorophyll/Liter per week. According to certain embodiments, the corresponding unmodified photosynthetic microalga is capable of producing a cumulative amount of from about 10 to about 100 milliliters of $H_2$ per 1 Liter culture comprising microalgae at a density of 10 mg chlorophyll/Liter per week.

According to certain exemplary embodiments, the genetically modified photosynthetic microalga is capable of producing a cumulative amount of from about 100 to about 700 milliliters of $H_2$ per 1 Liter culture comprising microalgae at a density of 10 mg chlorophyll/Liter per week.

According to certain embodiments, the LHCA2 comprises an amino acid sequence having at least 85% identity to the amino acid sequence set forth in SEQ ID NO:1.

According to certain embodiments, the LHCA2 comprises the amino acid sequence set forth in SEQ ID NO:1.

According to certain embodiments, the LHCA2 is encoded by LHCA2 having a nucleic acid sequence having at least 85% identity to the nucleic acid sequence set forth in SEQ ID NO:2.

According to certain embodiments, the LHCA2 is encoded by LHCA2 having the nucleic acid sequence set forth in SEQ ID NO:2.

According to certain embodiments, the PGR5 comprises an amino acid sequence having at least 65% identity to the amino acid sequence set forth in SEQ ID NO:3.

According to certain embodiments, the PGR5 comprises the amino acid sequence set forth in SEQ ID NO:3.

According to certain embodiments, the PGR5 is encoded by PGR5 having a nucleic acid sequence having at least 65% identity to the nucleic acid sequence set forth in SEQ ID NO: 4.

According to certain embodiments, the PGR5 is encoded by PGR5 having the nucleic acid sequence set forth in SEQ ID NO:4.

Any method as is known in the art to reduce the expression and/or activity of LHCA2 and PGR5 can be used according to the teachings of the present invention.

According to certain embodiments, the expression and/or activity of the LHCA2 and of the PGR5 is reduced by at least 25% compared to said LHCA2 and PGR5 activity in a corresponding unmodified photosynthetic microalga.

According to certain embodiments the expression and/or activity of the LHCA2 and the PGR5 is reduced to obtain null function proteins.

According to certain exemplary embodiments, the genetically modified photosynthetic microalga comprises LHCA2 encoding gene and PGR5 encoding gene, each comprising at least one mutation, wherein the mutation results in reduced expression and/or activity of the encoded LHCA2 and PGR5.

According to certain embodiments, the genetically modified photosynthetic microalgae is selected from any green microalgae which expresses hydrogenase. According to certain embodiments, the green microalga naturally expresses an endogenous hydrogenase. According to certain exemplary embodiments, the hydrogenase is [FeFe]-hydrogenase (HydA). According to certain alternative embodiments, the green microalga is further genetically modified to comprise hydrogenase synthetic operon comprising hydrogenase-assembly proteins.

According to certain embodiments, the growth conditions comprise growing the photosynthetic microalgae in a complete (non-starvation) growth medium; under ambient air; and, after about two hours of dark conditions, continuous growth under photosynthetic light. According to certain embodiments, the photosynthetic light is a continuous light. According to certain alternative embodiments, the photosynthetic light is pulsed light.

It is to be explicitly understood that the production of hydrogen by the genetically modified photosynthetic microalgae of the invention does not require growth under nutrient-deficient condition at any growth stage.

According to certain embodiments, the growth conditions comprise initial incubation of the microalgae in the dark for a time period of from about 1 hour to about 10 hours, thereafter exposing the microalgae to photosynthetic light. According to certain embodiments, the dark period is from about 1 hour to about 5 hours. According to certain exemplary embodiments, the dark period is of two hours.

According to certain embodiments, the intensity of the continuous photosynthetic light is in the range of from about 10 μE to about 10,000 μE (5 times full sun light). According to certain exemplary embodiments, the continuous light intensity is in the range of from about 50 μE to about 600 μE.

According to certain embodiments, the pulsed photosynthetic light is applied in cycles consisting of 1-20 msec of light followed by 100-500 msec dark. According to certain embodiments, the intensity of the pulsed light is above 500 μE and up to 10,000 μE.

Without wishing to be bound by any specific theory or mechanism of action, the light-dark cycles cease oxygen production while maintaining hydrogen production.

According to certain embodiments, the genetically modified photosynthetic microalgae is capable of producing at least 50, at least 55, at least 60, or more μmol $H_2$ per mg chlorophyll of said microalgae per hour.

According to certain embodiments, the genetically modified photosynthetic microalgae is capable of continuously producing at least 50 μmol $H_2$/mg Chl×h for at least 5 days, at least 10 days, at least 15 days or at least 20 days under photosynthetic light conditions. Each possibility represents a separate embodiment of the present invention.

According to certain embodiments, the genetically modified photosynthetic microalgae is capable of continuously producing at least 50 μmol $H_2$/mg Chl×h for at least 10 days.

According to certain embodiments, the genetically modified photosynthetic microalga is of the family Chlamydomonadaceae.

According to certain exemplary embodiments, the genetically modified photosynthetic microalga is *Chlamydomonas reinhardtii.*

According to certain embodiments, the genetically modified *C. reinhardtii* of the present invention comprises at least one insertion mutation in each of the lhca2 and pgr5 genes.

According to certain exemplary embodiments, the present invention provides a lhca2/pgr5 double-mutated *C. reinhardtii*, wherein the double-mutated *C. reinhardtii* produces at least 10 μmol $H_2$/mg Chl×h for at least 7 days when grown in a complete medium under ambient air conditions and about two hours of dark followed by exposure to light intensity of from about 60 μE to about 600 μE.

According to certain aspects, the present invention provides a process for bio-production of hydrogen, the process comprising (i) culturing genetically modified photosynthetic microalgae selected from the group consisting of microalgae having reduced expression and/or activity of PGR5 and microalgae having reduced expression and/or activity of PGR5 and LHCA2 in a complete medium under ambient air and exposure to dark period followed by exposure to light, wherein the light is at intensity enabling photosynthesis; and (ii) collecting hydrogen produced by the genetically modified photosynthetic microalgae.

Any system and growth vessels known for culturing photosynthetic microalgae can be used according to the teachings of the present invention. According to certain embodiments, the microalgae are grown in a photobioreactor (PBR). According to certain exemplary embodiments the entire growth period is performed within the same PBR. It is to be explicitly understood that the dark-light transition according to the process of the present invention does not interfere with the continuous growth of the cultured microalgae, typically maintained within a single vessel (e.g., PBR) throughout the entire growth period.

According to certain embodiments, the air within the culture growth vessel (e.g., PBR) is an atmospheric air or comprises the gas composition of atmospheric air. According to certain additional or alternative embodiments, the air within the growth vessel is flushed for a short period with pure nitrogen, argon or any other gas other than oxygen. It is to be understood that during the $H_2$ production according to the teachings of the present invention, the produced $H_2$ replaces the ambient air within the headspace of the bioreactor. The produced $H_2$ may be further transferred to and accumulated/stored within a separate reservoir. Any means for transferring the produced hydrogen to the reservoir and any vessel suitable for hydrogen storage area known in the art may be used.

According to certain embodiments, the process comprises culturing the genetically modified photosynthetic microalgae having reduced expression and/or activity of PGR5.

According to certain embodiments, the process comprises culturing the genetically modified photosynthetic microalgae having reduced expression and/or activity of PGR5 and LHCA2.

The PGR5 and LHCA2 proteins and polynucleotides encoding same are as described hereinabove.

The reduction of the activity and/or expression of each of PGR5 and LHCA2 is as described hereinabove.

According to certain embodiments, the dark period is from about 1 hour to about 10 hours. According to certain embodiments, the dark period is from about 1 hour to about 5 hours. According to certain exemplary embodiments, the dark period is of two hours.

According to certain embodiments, the exposure to light enabling photosynthesis comprises exposure to a continuous light. According to these embodiments, the genetically modified photosynthetic microalgae are exposed to photosynthetic light conditions for at least 5 days, at least 10 days, at least 15 days or at least 20 days. According to certain embodiments, the photosynthetic light intensity is from about 60 μE to about 600 μE.

According to certain embodiments, the exposure to light enabling photosynthesis comprises exposure to a pulsed light. According to these embodiments, light-dark pulses are applied. According to certain exemplary embodiments, the light-dark pulses comprise light pulses of 1-20 msec followed by dark pulses of 100-1000 msec. Light-dark pulses are typically applied when the photosynthetic light intensity is above 500 μE and up to 10,000 μE.

According to certain embodiments, the genetically modified photosynthetic microalgae produce hydrogen at a rate of at least 20 or more μmole $H_2$ per mg chlorophyll of said microalgae per hour. According to these embodiments, the $H_2$ production rate is maintained for at least 5 days, at least 10 days, at least 15 days or at least 20 days.

According to certain embodiments, the genetically modified photosynthetic microalgae is of the family Chlamydomonadaceae.

According to certain exemplary embodiments, the genetically modified photosynthetic microalga is *Chlamydomonas reinhardtii.*

It is to be understood that any combination of each of the aspects and the embodiments disclosed herein is explicitly encompassed within the disclosure of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 4 shows $H_2$ production by Δpgr5 over a period of 12 days under mixotrophic conditions.

FIG. 10A, 10E, 10I: ETR in oxic conditions. FIG. 10B, 10F, 10J: ETR in oxic conditions and in the presence of DCMU. FIG. 10C, 10G, 10K: ETR in anoxic conditions. FIG. 10D, 10H, 10L: ETR in anoxic conditions and in the presence of DCMU. Each time point is an average of at least three biological replicates (±SD) with statistical comparisons (the stars *) were analyzed by the student's test (p≤0.05).

Figure 1A:
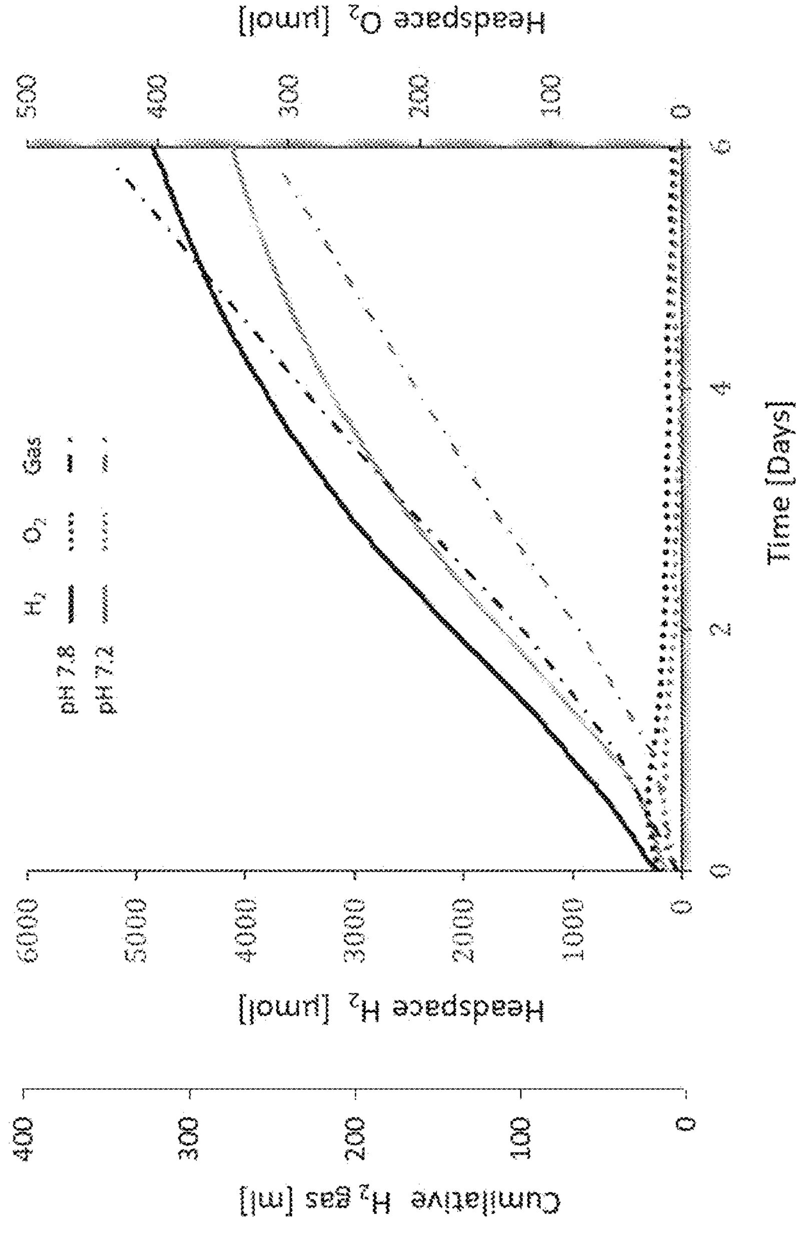
FIG. 1A shows cumulative gas, $H_2$ and $O_2$ amounts (ml) produced by the *C. reinhardtii* lhca2/pgr5 double mutant as a function of time at pH 7.2 and pH 7.8.

DETAILED DESCRIPTION OF THE INVENTION $BioH_2$ research is primarily converged into genetic manipulation and/or external engineering to effectuate the potential of $H_2$ production from microalgae. However, beyond a proof of concept by laboratory findings, transition to the industrial scales and demands must be made.

The present invention provides means and methods for bio-production of hydrogen in a continuous, cost-effective manner at amounts hitherto not reachable under large-scale manufacturing conditions. Specifically, the present invention provides genetically modified photosynthetic microalgae, particularly of the family Chlamydomonadaceae, the modification comprises reduced expression and/or activity of LHCA2 and PGR5. The present invention further discloses a process for $H_2$ bio-production comprising culturing the genetically modified photosynthetic microalgae of the invention, as well as a single PGR5 mutant under dark period followed by normal photosynthetic growth conditions that do not require nutrient deprivation, such that no steps of mass collection and medium replacement are required, nor growth under oxygen-deprived (anoxia) conditions.

Definitions

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office. Thus, any recitation that an embodiment "includes" or "comprises" a feature is a specific statement for sub embodiments "consist essentially of" and/or "consist of" the recited feature.

The term "about" as used herein refers to ±10%.

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region, and which are present on the mRNA, are referred to as 5' non-translated sequences. The sequences which are located 3' or downstream of the coding region, and which are present on the mRNA, are referred to as 3' non-translated sequences.

The terms "polynucleotide", "polynucleotide sequence", "nucleic acid sequence", and "isolated polynucleotide" are used interchangeably herein. These terms encompass isolated nucleotide sequences and the like. A polynucleotide may be a polymer of RNA or DNA or a hybrid thereof, that is single- or double-stranded, linear or branched, and that optionally contains synthetic, non-natural or altered nucleotide bases. The terms also encompass RNA/DNA hybrids.

As used herein, "sequence identity" or "identity" in the context of two nucleic acid or amino acid sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of (Henikoff and Henikoff 1992).

Identity (e.g., percent homology) can be determined using any homology comparison software, including for example, the BlastN software of the National Center of Biotechnology Information (NCBI) such as by using default parameters.

According to some embodiments of the invention, the identity is a global identity, i.e., an identity over the entire amino acid or nucleic acid sequences of the invention and not over portions thereof.

The terms "hydrogen" "molecular hydrogen" and $H_2$ are used herein interchangeably and refer to the diatomic gas $H_2$.

The term "photosynthetic microalga" or its plurality "photosynthetic microalgae" are used herein in their broadest scope and refer to unicellular microscopic eukaryotic algae capable of performing photosynthesis, typically found in freshwater and marine systems. Depending on the species, the microalgae size can range from a few micrometers (μm) to a few hundreds of micrometers. According to certain embodiments, the photosynthetic microalga or microalgae comprise at least one active hydrogenase. According to certain exemplary embodiments, the photosynthetic microalga or microalgae are of the family Chlamydomonadaceae, particularly a genetically modified *Chlamydomonas reinhardtii.*

As used herein, the term "corresponding" when used in regard to two or more photosynthetic microalga refer to microalga of the same species and of the same genetic background. According to certain embodiments of the present invention, corresponding photosynthetic microalgae differ in the expression of at least one protein and/or the polynucleotide encoding same. According to certain embodiments, the corresponding photosynthetic microalgae of the present invention differ in the expression of PGR5 and/or LHCA2 and/or the polynucleotides encoding same, wherein the unmodified microalga expresses unmodified, wilt type PGR5 and/or LHCA2.

The terms "Proton Gradient Regulation 5" and "PGR5" are used herein interchangeably and refer to a chloroplast protein involved in the regulation of the cyclic electron flow (CEF) around Photosystem I. It is essential for the reduction of PGRL1A by ferredoxin and for photoprotection. In a study of *Chlamydomonas reinhardtii* ΔATPase pgr5 and ΔrbcL pgr5 mutants it was shown to regulate cyclic electron flow under ATP- or Redox-limited conditions. (Johnson X. et al., 2014. Plant Physiol. 165, 438-452). The term further refers to the gene or parts thereof encoding the protein. The pgr5 mutation in the genetically modified algae used according to the teachings of the invention was generated by insertional mutagenesis as described in Johnson et al. (2014, ibid). According to certain embodiments, *Chlamydomonas* PGR5 (Cre05.g242400.t1.2) comprises the amino acid sequence set forth in SEQ ID NO:3 encoded by a polynucleotide comprising the nucleic acid sequence set forth in SEQ ID NO:4.

The term Light Harvesting Protein 2 (LHC2) refers to a peripheral antenna of PSI protein which together with LHCA9 is located to the opposite side of the LHCA belt. It was shown by Steinbeck et al. (Steinbeck J et al 2018. Proc Natl Acad Sci USA 115:10517-10522. DOI: 10.1073/pnas.1809973115) that detachment of LHC2 is a prerequisite for formation of a PSI-Cytb$_6$f super-complex. According to certain embodiments, *Chlamydomonas* LHC2 (Cre12.g508750.t1.2) comprises the amino acid sequence set forth in SEQ ID NO:1 encoded by a polynucleotide comprising the nucleic acid sequence set forth in SEQ ID NO:2.

The lhca2 mutant, designated as lhca2 LMJ.RY 0402109691, is derived from the *Chlamydomonas* CiLP library as described in Li et al. (Li X et al., 2016. Plant Cell 28, 367-387) and contains a DNA insertion in the second intron of the lhca2 nuclear gene. The double-mutant alga of the invention (Δpgr5/Δlhca2) was generated by crossing the single mutant Δpgr5 *C. reinhardtii* with the single mutant Δlhca2 *C. reinhardtii* and further backcrosses as described in the Example section hereinbelow.

As used herein, the expression and/or activity of PGR5 and/or LHCA2 according to the teaching of the invention is "reduced" or "inhibited" or "down regulated" or "knocked out" or "knocked down" if the level of the proteins or the polynucleotides encoding same, or the measured activity of the protein(s) is reduced by at least 30% compared to the level in a corresponding wild type photosynthetic microalga. According to certain embodiments, the level of the protein(s), the polynucleotide(s) encoding same or the protein(s) activity is reduced by at least 25%, at least 30%, at least 35%, at least 40%, at least 45%, at least 50%, at least 55%, at least 60%, at least 65%, at least 70%, at least 75%, at least 80%, at least 85%, at least 90% at least 95%, and more. According to some embodiments, the term "reduced expression" refers to undetectable amounts of the polynucleotide ending the protein. According to some embodiments, the term "reduced expression and/or activity" refers to 100% inhibition or "loss of function" or "null function" protein.

As used herein, the terms "ambient air" or "ambient air conditions" with reference to the growth conditions of the photosynthetic microalgae of the invention refer to natural atmospheric air or to air comprising the gas composition of atmospheric air under which the microalgae are grown. By volume, dry air contains 78.09% nitrogen, 20.95% oxygen, 0.93% argon, 0.04% carbon dioxide, and small amounts of other gases.

As used herein, the terms "complete" and "replete" with reference to a medium refers to medium suitable for mixotrophic culturing of photosynthetic microalgae comprising all the macro and micro nutrients which are needed for any plant/algae growth. The medium can be a liquid, porous polymeric matrices (e.g., alginate and nanocellulose), thin gels (agar) and the like. According to certain exemplary embodiments, Tris-Acetate buffer (TPA) is used as a complete medium.

The units "μmol photons $m^{-2}$ $s^{-1}$" and "$\mu Em^{-2}$ $s^{-1}$" are used herein interchangeably to describe light intensity.

According to certain aspects, the present invention provides a genetically modified photosynthetic microalga having reduced expression and/or activity of PGR5 and LHCA2 compared to the expression and/or activity of PGR5 and LHCA2 in a corresponding unmodified photosynthetic microalga.

According to certain embodiments, the genetically modified photosynthetic microalgae is capable of producing hydrogen at an amount at least 100-fold higher compared to the hydrogen production of the corresponding unmodified microalgae grown under the same growth conditions. According to certain aspects, the present invention provides a process for bio-production of hydrogen, the process comprising (i) culturing genetically modified photosynthetic microalgae selected from the group consisting of microalgae having reduced expression and/or activity of PGR5 and microalgae having reduced expression and/or activity of PGR5 and LHCA2 in a complete medium under ambient air and exposure to dark period followed by exposure to light, wherein the light is at intensity enabling photosynthesis; and (ii) collecting hydrogen produced by the genetically modified photosynthetic microalgae.

According to certain embodiments, the genetically modified photosynthetic microalgae has reduced expression of a PGR5 encoding polynucleotide and/or reduced expression and/or activity of the encoded PGR5.

According to certain embodiments, the genetically modified photosynthetic microalgae has reduced expression of am LHCA2 encoding polynucleotide and/or reduced expression and/or activity of the encoded According to certain embodiments, the genetically modified photosynthetic microalgae has reduced expression of a PGR5 encoding polynucleotide and/or reduced expression and/or activity of the encoded PGR5.

Two major challenges limit efficient biological $H_2$ production. The first challenge is to overcome the inactivation of the hydrogenase enzyme, which serves as a hydrogen production catalyst, by molecular oxygen ($O_2$) produced during photosynthesis. The second challenge is to overcome the limited electron flow from the photosynthetic apparatus to the hydrogenase enzyme.

In order to engineer photosynthetic electron-transfer in the green alga *Chlamydomonas reinhardtii* for improvement of $H_2$ production, an increased respiration in the pgr5 mutant served as a starting point. The pgr5 mutant exhibits increased respiration due to a shortage in ATP production in the chloroplast, which signals the mitochondria to operate intensively. ATP shortage in the chloroplast allows not only maintaining a local anoxia under ambient conditions, but it also suppresses the main competitor of the $H_2$ production process, $CO_2$ fixation via the Calvin cycle. However, while photosynthetic microalgae genetically modified to have reduced activity of PGR5 produce significantly higher $H_2$ amounts compared to corresponding unmodified microalgae, a further increase in the $H_2$ amounts is desired for a more cost-effective large-scale production.

In order to further enhance the electron flow to H2 production, formation of a supercomplex containing key components of the photosynthetic electron transfer chain: photosystem I (PSI), cytochrome bof and FNR (PSI-Cyt$b_6$f-FNR super-complex) and/or PSI dimer was attempted. Without wishing to be bound by any specific theory or mechanism of action, these super-complexes may allow cyclic electron flow (CEF) around PSI and might be involved in partitioning of electrons at the acceptor side of PSI, and thus being involved in the boost of total electron output and improved H2 production. It has been suggested that unbinding of LHCA2 and LHCA9 is required for PSI-Cyt$b_6$f super-complex formation (Steinbeck J et al 2018, ibid). Recently, it was indicated that the absence of LHCA2 could also lead to the formation of PSI-dimers (Naschberger A et al., 2021 bioRxiv preprint doi: https://doi.org/10.1101/2021.08.30.458224).

In order to test genetic interaction between pgr5 and lhca2, the pgr5 and lhca2 mutant strains were crossed to produce the pgr5/lhca2 double mutant of the invention, designated herein *Chlamydomonas elsa*. The *C. elsa* addressed both challenges described above, being capable of fast and efficient $H_2$ production for periods exceeding 14 days. Furthermore, *C. elsa* is robust and performs well at temperatures up to 35° C.-36° C. and/or under high light intensity of 250 μE to 600 μE. Thus, the single (pgr5) mutant strain and the double (pgr5 and lhca2) mutant strain of the invention offer an alternate strategy for hydrogen production. The alternative strategy enables use of sunlight and abundant resources (e.g., uncultivated soil, wastewater or seawater) and accordingly reduces competition with agricultural resources. Alternatively, or additionally, the native replication rate of photosynthetic microalgae, particularly of the family Chlamydomonadaceae, allows rapid and cost-effective implementation of solar bio-factories producing $H_2$.

According to certain embodiments, the LHCA2 comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to the amino acid sequence set forth in SEQ ID NO:1. Each possibility represents a separate embodiment of the present invention.

According to certain embodiments, the LHCA2 is encoded by LHCA2 having a nucleic acid sequence having at least at least 85%, at least 86%, at least 87%, at least 88%, at least 89%, at least 90%, at least 91%, at least 92%, at least 93%, at least 94%, 95%, at least 96%, at least at least 97%, at least 98%, at least 99% or 100% identity to the nucleic acid sequence set forth in SEQ ID NO:2. Each possibility represents a separate embodiment of the present invention.

According to certain embodiments, the PGR5 comprises an amino acid sequence having at least 65%, at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to the amino acid sequence set forth in SEQ ID NO:3. Each possibility represents a separate embodiment of the present invention.

According to certain embodiments, the PGR5 is encoded by PGR5 having a nucleic acid sequence having at least 65%, at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to the nucleic acid sequence set forth in SEQ ID NO:4. Each possibility represents a separate embodiment of the present invention.

According to certain embodiments, the genetically modified photosynthetic microalga is selected from any green microalgae which expresses hydrogenase, particularly [FeFe]-hydrogenase. According to certain embodiments, the green microalga naturally expresses the hydrogenase. According to certain alternative embodiments, the green microalga is genetically modified to comprises within the nucleus or the chloroplast at least one polynucleotide encoding hydrogenase synthetic operon comprising hydrogenase-assembly proteins. According to certain embodiments, the polynucleotide encodes a hydrogenase operon of a eukaryotic origin. According to these embodiments, the hydrogenase-assembly proteins comprise a HydEF protein having at least 50% identity to HydEF UniProtKB Accession No. Q6PSL5 and HydG to having at least 50% identity to HydG UniProtKB Accession No. Q6PSL4. According to certain embodiments, the polynucleotide encodes a hydrogenase operon of a prokaryotic origin. According to these embodiments, the hydrogenase-assembly proteins comprise a HydE protein having at least 50% identity to HydE UniProtKB Accession No. A0A7Y9AEX4; HydF protein having at least 50% identity to HydF UniProtKB Accession No. A0A7X1AEP6; and HydG to having at least 50% identity to HydG UniProtKB Accession No. A0A7Y9AFT2.

According to certain embodiments, the expression and/or activity of the LHCA2 and/or of the PGR5 is reduced by at least 25%, at least 30%, at least 35%, at least 40%, at least 45%, at least 50%, at least 55%, at least 60%, at least 65%, at least 70%, at least 75% at least 80% at least 85% at least 86% at least 87% at least 88% at least 89% at least 90% at least 91% at least 92% at least 93% at least 94% at least 95% at least 96% at least 97% at least 98% at least 99% or more compared to said LHCA2 and/or PGR5 expression and/or activity in a corresponding unmodified photosynthetic microalga. Each possibility represents a separate embodiment of the present invention.

According to certain embodiments the expression and/or activity of the LHCA2 and/or the PGR5 is reduced to obtain null function protein.

Down-regulation or inhibition of LHAC2 and/or PGR5 expression can be affected at the genomic and/or the transcript level by mutations (including deletions, insertions, site specific mutations including nucleotide substitution and the like, as long as the mutation(s) result in down-regulation of the gene expression or in the production of less-functional or non-functional protein); using a variety of molecules that interfere with transcription and/or translation (e.g., antisense, siRNA, Ribozyme, or DNAzyme); or at the protein level using, e.g., antagonists, enzymes that cleave the polypeptide, and the like.

According to certain exemplary embodiments, down-regulation or inhibition of LHAC2 and/or PGR5 expression is affected by mutagenesis. Any method for mutagenesis as is known in the art can be used according to the teachings of the present invention including chemical mutagenesis, radio-mutagenesis and site directed mutagenesis, for example using genome editing techniques.

According to certain exemplary embodiments, the pgr5 mutation may be generated by DNA insertional mutagenesis as described, for example, in Dent et al., 2005 (Dent R M et al., 2005. Plant Physiol 137, 545-556) with linearized pBC1 plasmid encoding paromomycin resistance as described in Tran et al., 2012 (Tran PT, 2012. PLOS ONE 7: e42196).

According to certain exemplary embodiments, the lhca2 mutation is derived from the *Chlamydomonas* CiLP library as described in Li et al. (Li X et al., 2016. ibid and contains a DNA insertion in the second intron of the lhca2 nuclear gene.

The growth conditions required for supporting the significant $H_2$ production by the double mutant Δlhca2/Δpgr5 of the present invention, as well as by the single mutant Δpgr5, although to a lower extent, according to the process of the present are adequate for large-scale production and typically require photobioreactors and common microalgae culture medium.

According to certain embodiments, the growth conditions comprise growing the photosynthetic microalgae in a complete (non-starvation) growth medium under ambient air in the dark and thereafter exposing the microalgae culture to light at an intensity enabling photosynthesis.

According to certain embodiments, the photosynthetic microalgae are grown in the dark for a period of from about 1 h to about 10 h. According to certain embodiments, the photosynthetic microalgae are grown in the dark for a period of from about 1 h to about 9 h, from about 1 h to about 8 h, from about 1 h to about 7 h, from about 1 h to about 6 h, from about 1 h to about 5 h, from about 1 h to about 4 h, from about 1 h to about 3 h, or from about 1 h to about 2 h. Each possibility represents a separate embodiment of the present invention.

According to certain exemplary embodiments, photosynthetic microalgae are grown in the dark for two hours.

According to certain embodiments, the light enabling photosynthesis to which the microalgae are exposed after the dark period is a continuous light. According to these embodiments, the intensity of the continuous photosynthetic light is in the range of from about 10 μE to about 10,000 μE (5 times full sun light). According to certain embodiments, the intensity of the continuous photosynthetic light is in the range of from about 10 μE to about 5000 μE, or from about 10 μE to about 1000 μE. Each possibility represents a separate embodiment of the present invention. According to certain exemplary embodiments, the continuous light intensity is in the range of from about 50 μE to about 600 μE.

According to certain embodiments, the light enabling photosynthesis to which the microalgae are exposed after the dark period is applied in pulses ("pulsed light"). According to certain embodiments, the pulsed photosynthetic light is applied in cycles consisting of 1-20 msec of light followed by 100-500 msec dark. According to certain embodiments, the intensity of the pulsed light is above 500 μE and up to 10,000 μE. According to certain embodiments, the intensity of the pulsed light is above 500 μE, the intensity of the pulsed light is above 1000 μE, above 1500 μE, or above 2000 μE. Each possibility represents a separate embodiment of the present invention. According to certain exemplary embodiments, the intensity of the pulsed light is about 2,500 μE.

According to certain embodiments, the genetically modified photosynthetic microalgae is capable of producing at least 10, at least 15, at least 20, at least 25, at least 60 or more μmol $H_2$ per mg chlorophyll of said microalgae per hour.

According to certain embodiments, the genetically modified photosynthetic microalgae is capable of continuously producing at least 10 μmol, at least 15 μmol, at least 20 μmol, at least 25 μmol, at least 30 μmol, at least 35 μmol, at least 40 μmol, at least 45 μmol, or at least 50 μmol, or at least 50 μmol $H_2$/mg Chl×h for at least 5 days, at least 10 days, at least 15 days or at least 20 days under photosynthetic light conditions according to the process of the invention. Each possibility represents a separate embodiment of the present invention.

According to certain embodiments, the genetically modified photosynthetic microalgae is of the family Chlamydomonadaceae.

According to certain exemplary embodiments, the genetically modified photosynthetic microalga is *Chlamydomonas reinhardtii*. According to certain exemplary embodiments, the genetic background of the genetically modified *C. reinhardtii* is of a cc124/125 strain.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Methods

Cell Growth and Conditions

In Bio$H_2$ research, as in other fields, laboratory findings may fail to extrapolate into large-scale use, and in the case of microalgae, into agriculture/industrial set-ups. This challenge is heightened for photosynthetic products, since many different variables like culture density and light permeability can dramatically affect productivity and consequently, ultimately fail in the commercial production phase. Accordingly, the experiments of the present invention have been conducted directly on a large measurement system, a 1-L photobioreactor (PBR, BlueSens) with built-in probes for the analysis of various parameters such as $O_2$ and $H_2$ concentration, gas output, culture pH and optical density.

Mutant and control *Chlamydomonas* strains were cultivated in replete Tris-Acetate (TAP) medium, kept in Erlenmeyer flasks at constant stirring, under irradiation of ~60 HE $m^{-2}$ $s^{-1}$ at 24° C. For experimental procedures, cells were diluted to a fresh TAP medium to reach the next day's cultures at early log phase (2-5 μg Chl $ml^{-1}$). Chlorophyll was extracted and determined according to Jeffery and Humphrey (Jeffrey, S. W. & Humphrey, G. F. Biochem. und Physiol. der Pflanz. 167, 191-194, 1975). The cell starter was transferred to grow in 1-L TAP medium to reach a chlorophyll concentration of ~10 μg/ml and then transferred into 1-L BlueSens PBR. Each bioreactor was supplemented with 1 ml acetic acid (16.7 M) and tittered to the desired pH using NaOH. The bioreactors were placed on a Digital Hot-Plate Stirrer (Witeg) and kept at 30° C. with constant stirring of 800 rpm. Dark/light regime was applied as described below. The percentages of $O_2$ and $H_2$ in the bioreactor's headspace were measured using thermal conductivity (TCD) sensors (BCP, BlueSens gas sensor GmbH), and $H_2$ gas (ml) output was monitored using Blue Vcount gas counters (BlueSens).

Mass Inlet Membrane Spectroscopy (MIMS) Analysis for $H_2$ or $CO_2$ Exchange

MIMS analysis was performed as described in Liran Et al. (Liran, O. et al. Plant Physiol. 172, 264-271, 2016). For $H_2$ or $CO_2$ measurements, 5 ml of 15 or 45 μg Chl/ml in TAP supplemented with (4-(2-hydroxyethyl)-1-piperazineethanesulfonic acid) (HEPES) (50 mM) cells were placed in a cuvette and fitted into a metabolic chamber (Optical unit ED-101US/MD, Walz). Following 2 or 1 hr dark incubation, the cells were exposed to 370 or 2500 μE $m^{-2}$ $s^{-1}$ of a red actinic light using a Dual-Pulse Amplitude Modulated Fluorometer (DUAL-PAM-100; Heinz Walz Gmbh, Effeltrich, Germany). If stated, DCMU (200 μM, Merck S279013) or hydroxylamine (HA, 1 mM) were added 10 min before light exposure. Masses were detected using a 0.5 second dwelling time per mass. Based on a standard curve described in Liran et al. (ibid), conversion factors were applied to normalize $H_2$ and $CO_2$ traces.

Measurements of Photosynthetic Electron Transfer Rates (ETR)

For determining the ETR, the electrochromic shift (ECS) signals were measured using a Joliot-type spectrophotometer (JTS-10, Biologic). In brief, all absorption changes were normalized to the ECS ΔI/I signal (520-nm-546-nm) produced after a saturating laser flash in the presence of 1 mM hydroxylamine (HA) and 10 μM 3-(3,4-dichlorophenyl)-1,1-dimethylurea (DCMU). Thus, the flash-induced rapid ECS describes the density of active PSI centers in PSII-inhibited HA/DCMU samples (measured as 1 charge separation·$PSI^{-1}$). The ECS was also deconvoluted using the dark pulse method (DIRK) (reviewed in Bailleul et al., 2010. Photosynthesis Research 106, 179-189; Joliot and Joliot, 2002. Proc Natl Acad Sci USA 99, 10209-10214; and Nawrocki et al., 2019. Biochim Biophys Acta Bioenerg 1860, 425-432) and electron transfer rates were calculated. The ECS signal were induced by continued illumination was measured by DIRK measurement in band shift at absorption 520 nm and 546 nm. The first light phase 1 of DIRK in 10 s illumination period followed by 700 msec short dark-adapted and the second light phase 2 of DIRK during a 10 s illumination.

Example 1: *Chlamydomonas* Strains Used in the Study

Figure 3:
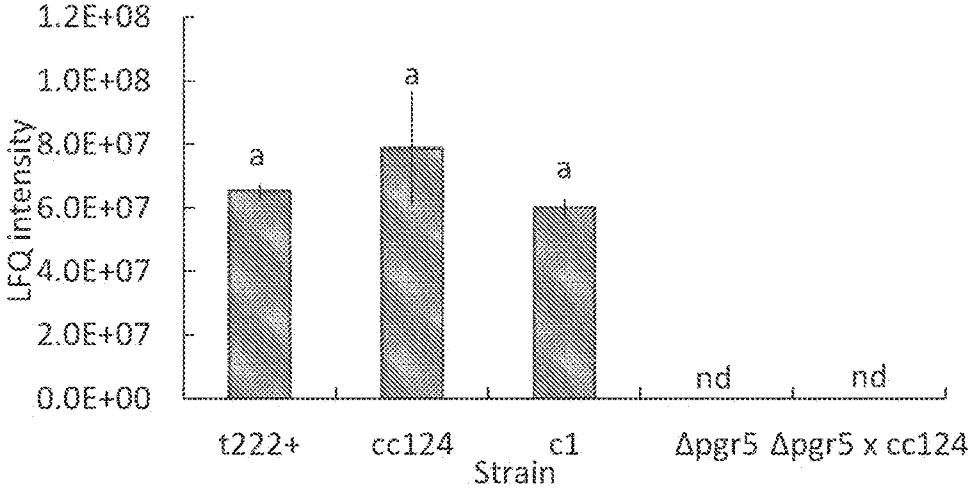
FIG. 3 shows PGR5 protein abundances determined via LFQ (label-free quantitation) in WT t222+, WT cc124, c1, Δpgr5, and Δpgr5xcc124 mutants.

Wild type (wt) *Chlamydomonas* strains are available from in the *Chlamydomonas* collection: chlamycollection.org. Wild type strain t222+ and cc124 were used as controls during the study of the present invention.

pgr5 mutant (Δ pgr5) was produced as previously described by an inventor of the present invention and co-workers (Johnson et al., 2014, ibid). The mutation is an insertion mutation. As is shown in FIG. 3, no detectable amount of PGR5 could be observed, as verified by mass spectrometry-based peptide and protein quantification. The original pgr5 mutant produced in the background of T22 was backcrossed into the wild type cc124/125 to obtain pgr5 cc124/125. pgr5 control (c1) is a rescue strain of Δpgr5 complemented with the wt copy of the gene that accumulates ~100% of wt PGR5 levels, produced as described in Johnson et al. (2014, ibid).

lhca2 mutant (Δlhca2) designated as lhca2 LMJ.RY 0402109691, is derived from the *Chlamydomonas* CiLP library as described in in Li et al. (2016. ibid). The mutation was inserted in the background of the strain cc4533.

pgr5/lhca2 mutant (Δpgr5/Δlhca2) designated as *C. elsa*, was produced via cross between pgr5 t222 and lhca2 cc4533.

Figure 5A:
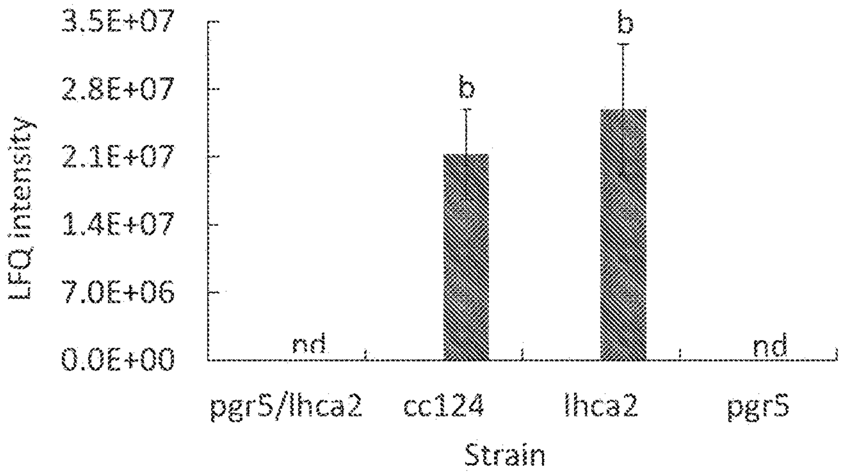
FIG. 5 shows PGR5 and LHCA2 protein abundances determined via LFQ (label-free quantitation) in WT cc124, Δlhca2, Δpgr5xcc124 and Δpgr5/Δlhca2 mutants.
Figure 5B:
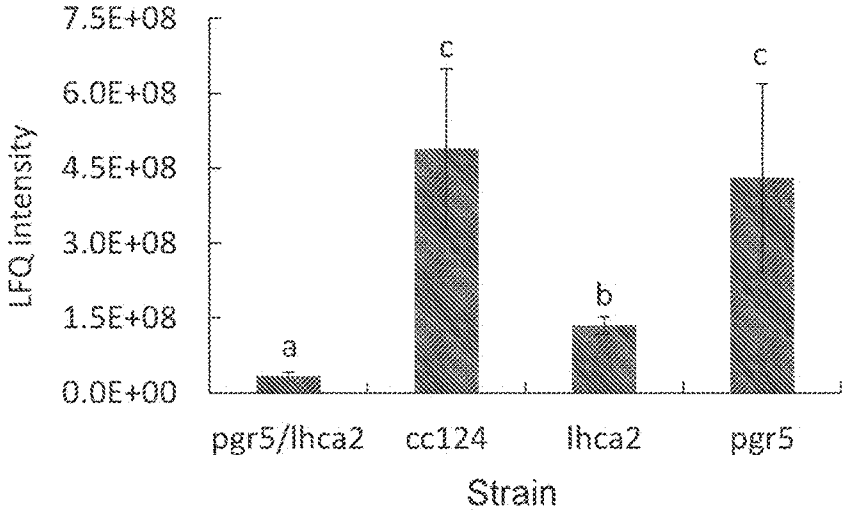

In an independent experiment lhca2 and pgr5 single mutants described above were genetically backcrossed three times using WT cc124/cc125 cells. After successful backcrosses, a pgr5/lhca2 mutant was generated by additional rounds of genetic crossings. The mutant status was verified by mass spectrometry-based peptide and protein quantification (FIG. 5). This was done to compare the $H_2$ production performances in single and double mutants in comparable genetic backgrounds.

Figure 1B:
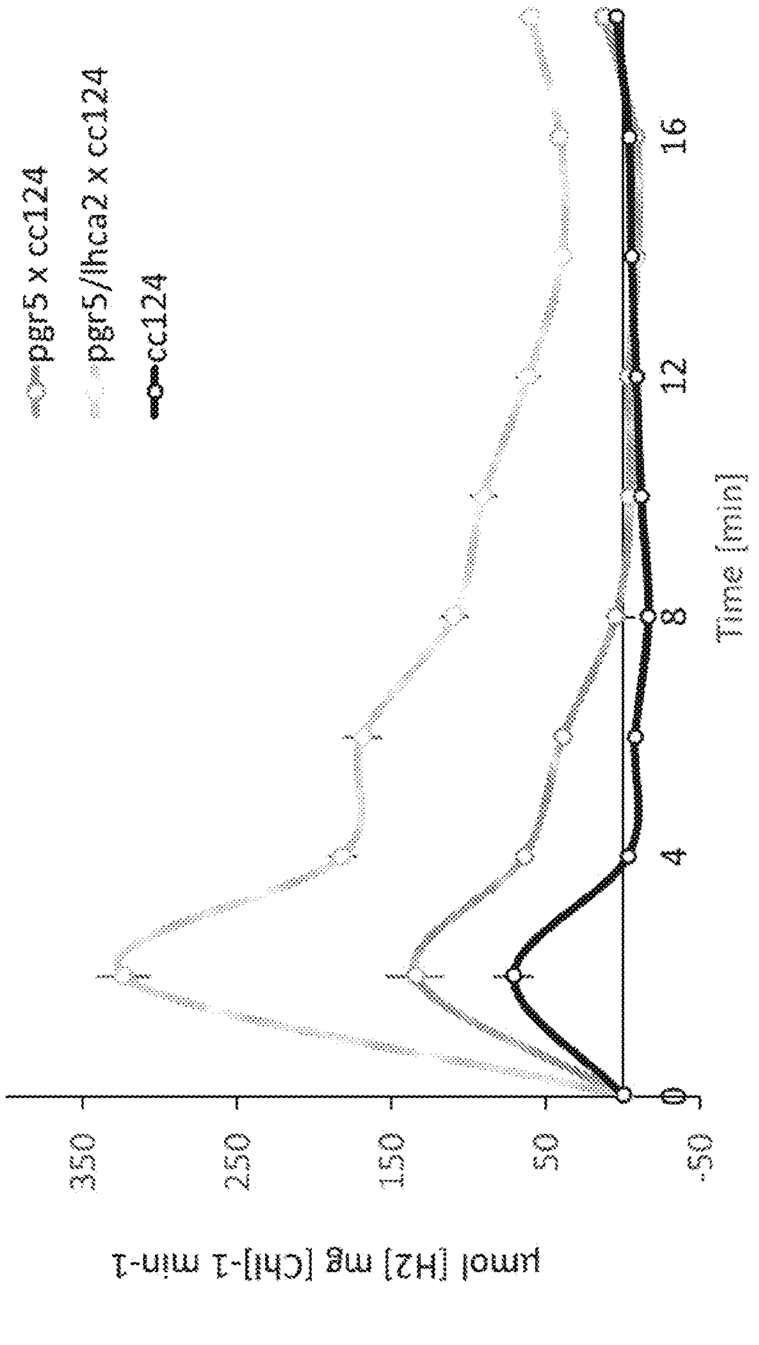
FIG. 1B shows $H_2$ production rate (μmol $H_2$×mg $chl^{-1}$× $min^{-1}$) by the *C. reinhardtii* lhca2/pgr5 double mutant compared to $H_2$ production by the single mutant pgr5, both in the background of cc124, and of the wt strain cc124.
Figure 2:
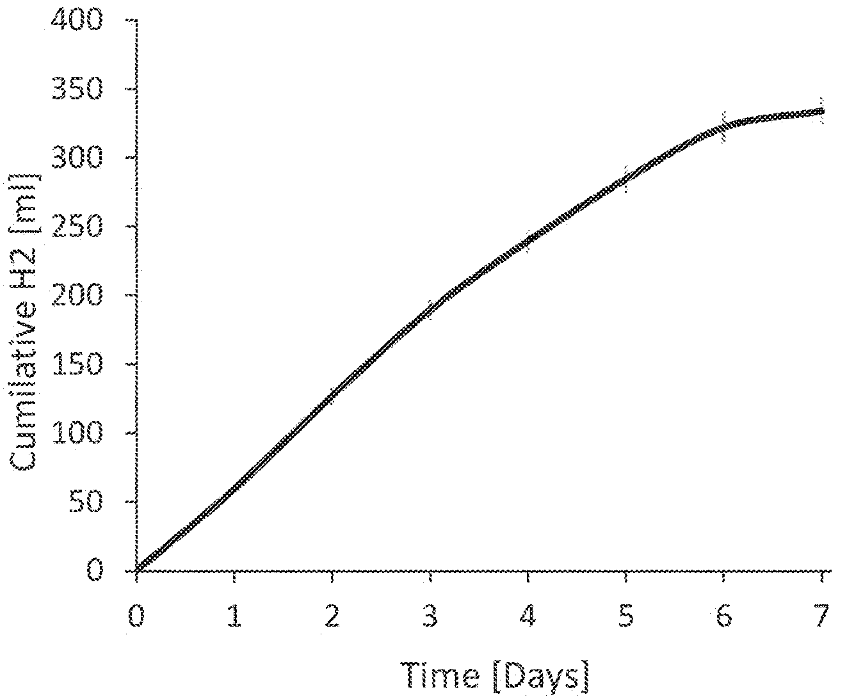
FIG. 2 shows $H_2$ accumulation at 32° C. of lhca2/pgr5 double mutant in the PBR system shown in FIG. 7.

Example 2: $H_2$ Production Under Replete Medium Conditions by the pgr5/lhca2 Mutant $H_2$ production by the pgr5/lhca2 mutant (*C. elsa*) of the invention was tested under nutrient replete Tris-Acetate (TAP) and oxic growth conditions. A culture at a density of 10 mg chlorophyll per Liter was poured into 4×1 Liter photobioreactors (PBR, BlueSense) and the head space of the 4×PBRs setup was sparged once with nitrogen for 1 minute. Then, the PBRs were kept in darkness for 2 hours after which irradiance was turned on at 400 μE. The bioreactors were continuously monitored for gas concentration using $H_2$ and $O_2$ detectors while gas accumulation at the bioreactor headspace was recorded using a Ritter's gas volume analyzer. During the experiments, excess of $H_2$ produced was released to the atmosphere Notably, while $O_2$ accumulation is negligible due to enhanced respiration in the newly engineered pgr5/lhca2 mutant strain (*C. elsa*), $H_2$ production started immediately after the onset of irradiation (FIG. 1A, under pH=7.2 (gray lines) and pH=7.8 (black lines) nutrient replete TAP conditions). $H_2$ production rate (μmol $H_2$ mg Chl-1 $min^{-1}$) by the pgr5/lhca2 double mutant was significantly higher from the production rate obtained by the single mutant pgr5. Both mutant are with the genetic background of cc124 (FIG. 1B). In addition, a cumulative $H_2$ production by *C. elsa* over time is shown in FIG. 2 (an average of 4 biological repeats using a culture at a density of 10 mg chlorophyll per Liter).

Figure 4A:
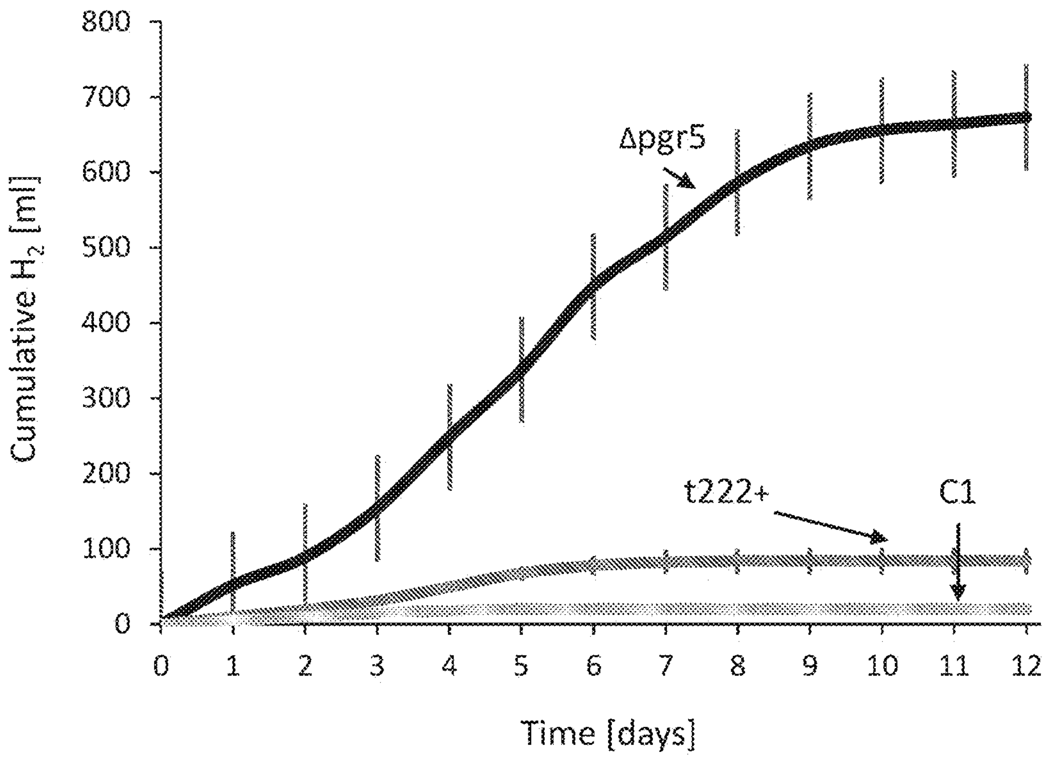
FIG. 4A: $H_2$ gas (ml) accumulated in the headspace of bioreactors (BlueSens), measured by BlueVCount gas counters. 1 L of culture at a concentration of 10 μg Chl/ml was subjected to 2 hr dark incubation followed by 12 days of continuous illumination at 350 μmol photons $m^{-2}$ $s^{-1}$. Mean values and standard error bars are shown (n=4).
Figure 6:
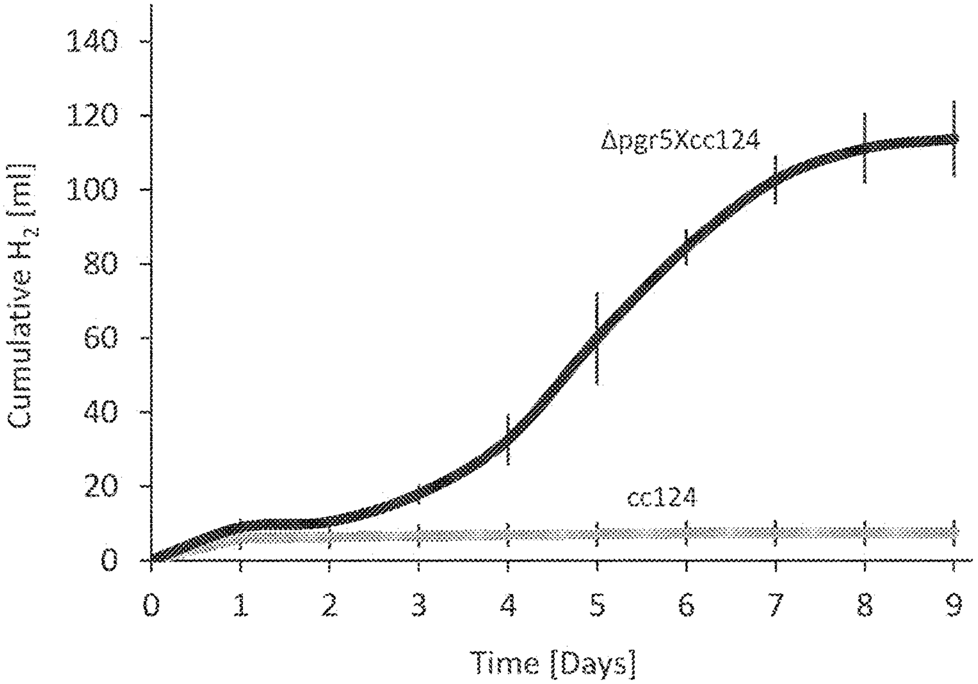
FIG. 6 shows that Δpgr5 xcc124 cells produce $H_2$ for extended periods under mixotrophic conditions. $H_2$ gas (ml) accumulated in the headspace of bioreactors (BlueSens), measured by BlueVCount gas counters. 1 L of Δpgr5xcc124 or cc124 cells, at a concentration of 5-8 μg Chl/ml were subjected to 2 hr dark incubation followed by a continuous illumination at 400 μmol photons $m^{-2}$ $s^{-1}$. A burst of $H_2$ production occurred in both strains within a few minutes, but only in Δpgr5xcc124 cells, $H_2$ accumulation remained for several days. Error bars are in SE (n=4, for each strain).

Example 3: $H_2$ Production Under Replete Medium Conditions by the Por5 Mutant $H_2$ production by the *C. reinhardtii* single Δpgr5 mutant under an ambient mixotrophic setting was compared to the $H_2$ production by its parental wt strain t222+ and to a rescue strain of Δpgr5 complemented with the wt copy of the gene that accumulates ~100% of wt PGR5 levels (c1) (FIG. 3). Δpgr5 continuously produced $H_2$ over the entire measurement period (12 days), and over 670 ml of 100% $H_2$ gas were accumulated by this phenotype (FIG. 4A). Moreover, in some days, the average $H_2$ production rate reached 18.5 μmol $H_2$ mg $Chl^{-1}$ $h^{-1}$ (Table. 1). These results show for the first time that a single Δpgr5 mutant of *C. reinhardtii* can produce significant amounts of $H_2$ under mixotrophic conditions without the need for sulfur starvation. Interestingly, under the current experimental conditions (cell density of 10 μg chl $ml^{-1}$ and light intensity of 350 μmol photons $m^{-2}$ $s^{-1}$), the parental control strain (t222+) and the complemental strain (c1) did not accumulate a significant amount of $O_2$ as well. Without wishing to be bound by any specific theory or mechanism of action, the low $O_2$ may be the cause for the moderate trace accumulation of $H_2$ by the wt and c1 strains for few days (FIG. 4A), indicating that competition with Calvin cycle activity is the main bottleneck for $H_2$ production. The ability of PGR5's mutation to mediate an extended $H_2$ production phenotype was confirmed following a back-cross to the wild-type strain cc124 (Δpgr5 X cc124) by a long-term $H_2$ production assay (BlueSens bioreactors, FIG. 6). Following light exposure, an altering lag time for respiration was needed (based on the strain's $O_2$ evolving machinery), after which cells accumulated $H_2$ over 9 days. Nonetheless, these results indicate that PGR5 mutation allows long-term mixotrophic $H_2$ production. Yet, the extent of this duration is also dependent on the genetic background of the respective wild type.

Figure 4B:
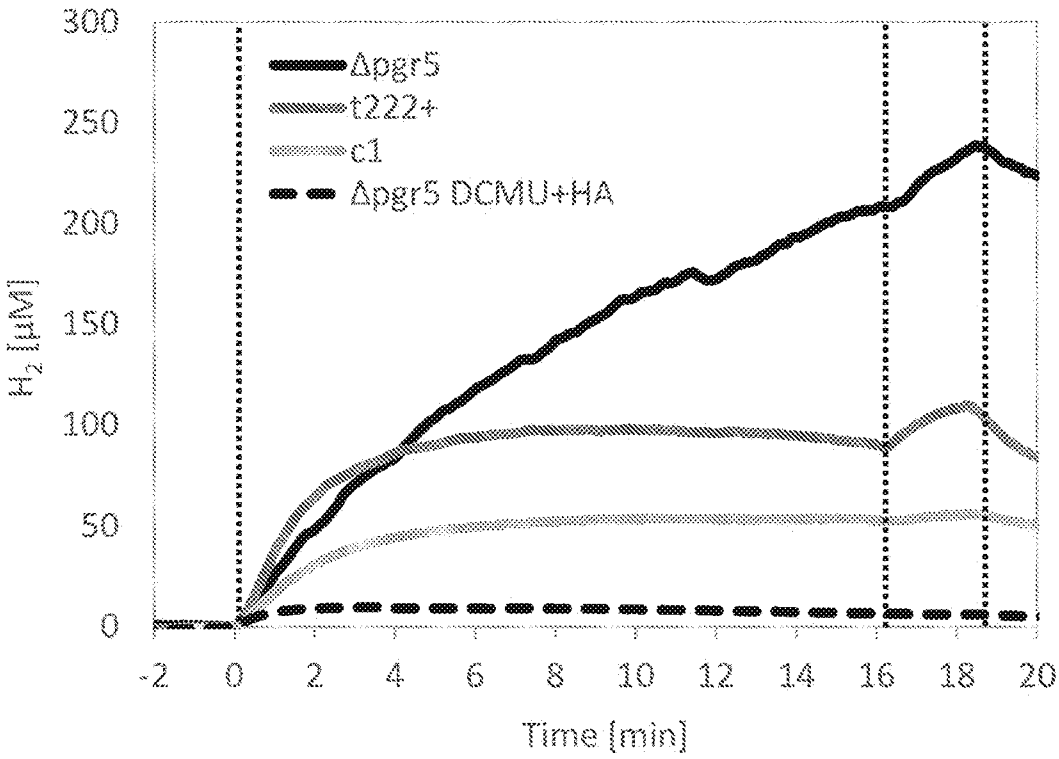
FIG. 4B: Short-term kinetics of dissolved $H_2$ in t222+, c1 and Δpgr5 (with or without PSII inhibition [dashed/solid lines, respectively]), measured by MIMS. Following 1 hr of dark incubation, cells were illuminated continuously under an irradiance of 370 μE $m^{-2}$ $s^{-1}$ for 16 min (white background) and additional 2 min of maximal light intensity (light gray background). Mean values are shown (n=4).

To gain further insights on the kinetics of $H_2$ production, the short-term accumulation of $H_2$ in Δpgr5 was compared with t222+ and c1 using a membrane inlet mass spectrometer (MIMS) (FIG. 4B, solid lines). Following 1 h of dark anaerobic incubation, the cells were exposed to red actinic irradiance at 370 μmol photons $m^{-2}$ $s^{-1}$ and dissolved $H_2$ was measured for 16 min. t222+ demonstrated a typical kinetic profile of wt strains with a short burst of $H_2$ production, followed by a decay once the Calvin cycle has been activated (~1 min). Δpgr5 cells exhibited a steady accumulation of $H_2$ (solid line), consistent with the BlueSens measurements, as well as the c1 complement strain, which restored the wt kinetics. It was estimated that in a wt strain, there would be a relatively large pool of non-reduced HydA's, due to electrons shift towards carbon fixation. In order to examine this hypothesis, the light intensity was increased to 2500 μmol photons $m^{-2}$ $s^{-1}$ after 16 minutes; this allowed to observe the full reduction potential of HydA in these clones. Although all three strains increased their $H_2$ production as a result of light intensification, the wt clone t222+ demonstrated the most dramatic shift, indicating that it contains a larger idle pool of HydA, due to electrons routed in favor of $NADP^+$ reduction by FNR. These results imply that in Δpgr5, there is a perpetual divergence of electrons to HydA. To verify that $H_2$ production is fueled by electrons originated from water-splitting, inhibitors that block electron transfer from PSII, 3-(3,4-Dichlorophenyl)-1,1-dimethylurea (DCMU) and Hydroxylamine (HA) were added. The results clearly show that under PSII inhibition, $H_2$ barley accumulates, denoting PSII as the major source of electrons for $H_2$ production in Δpgr5 (FIG. 4B, dashed line).

Like other mutants strains, Δpgr5 was isolated via random insertional mutagenesis to the nucleus, often resulting in unpredicted loci of multiple inserts, which could outcome with different phenotypes without direct causality between observable characteristics and one exact gene knockout. Therefore, the restoration of PGR5 expression in c1 (shown by mass-spectrometric (MS) analyses (FIG. 3)) along with its re-gaining of the wild-type phenotype in both measurements is of crucial importance as it links the PGR5 mutation to this strain's ability to maintain prolonged $H_2$ production. A significant finding is the difference between small-scale (MIMS, 5 ml) and large-scale (BlueSens, 1 L) experiments exemplified by the ~2-min $H_2$ production phenotype of t222+ and c1 that has been seemingly lost upon transition to large-scale measurement, a phenomenon that has not been observed for the Δpgr5 mutant, emphasizing its suitability for a large scale $H_2$ production (data not shown).

TABLE 1

Average $H_2$ Production rates (μmol $H_2$ mg $Chl^{-1}h^{-1}$) per day

| | Average $H_2$ Production rates (μmol $H_2$ mg $Chl^{-1}h^{-1}$) per day Day | | | | | |
|---|---|---|---|---|---|---|
| Strain | 1 | 2 | 3 | 4 | 5 | 6 |
| Δpgr5 | 8.8 ± 5.0 | 6.2 ± 1.0 | 10.9 ± 1.4 | 15.9 ± 2.7 | 15.0 ± 2.8 | 18.5 ± 2.7 |
| t222+ | 1.7 ± 0.2 | 1.6 ± 0.4 | 2.1 ± 0.3 | 3.0 ± 0.7 | 3.1 ± 0.8 | 1.7 ± 0.7 |
| c1 | 0.8 ± 0.2 | 0.8 ± 0.5 | 0.8 ± 0.4 | 0.6 ± 0.2 | 0.3 ± 0.2 | 0 |

TABLE 1-continued

| Average $H_2$ Production rates (μmol $H_2$ mg $Chl^{-1}h^{-1}$) per day | | | | | | |
|---|---|---|---|---|---|---|
| | Average $H_2$ Production rates (μmol $H_2$ mg $Chl^{-1}h^{-1}$) per day) Day | | | | | |
| Strain | 7 | 8 | 9 | 10 | 11 | 12 |
| Δpgr5 | 11.0 ± 2.5 | 12.1 ± 0.9 | 8.1 ± 0.5 | 3.5 ± 1.2 | 1.4 ± 0.6 | 1.5 ± 1.2 |
| t222+ | 0.8 ± 0.5 | 0.2 ± 0.1 | 0 | 0 | 0 | 0 |
| c1 | 0 | 0 | 0 | 0 | 0 | 0 |

Average hydrogen production rates (μmol $H_2$ mg $Chl^{-1}h^{-1}$]) were calculated over 12 days and averaged per day. The rates were analyzed from the $H_2$ gas accumulated in BlueSens bioreactors' headspace and measured by the BlueVCount gas counter. Mean values (n=4) and ±SE are shown.

Figure 11A:
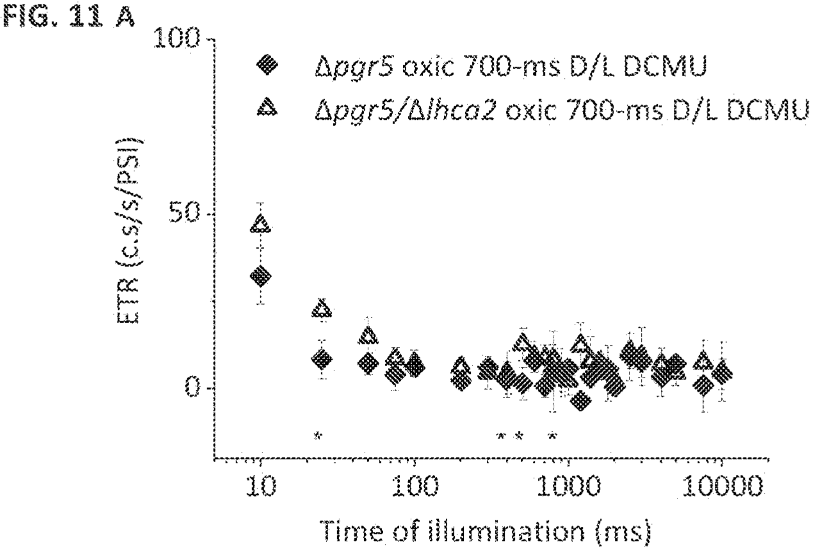
FIGS. 11A-11B show a comparison of ETR measured in pgr5/lhca2 and pgr5 in oxic (FIG. 11A) and anoxic conditions (FIG. 11B) after DCMU treatment. The data are taken from the second consecutive ETR measurement (after a 700 (msec) short dark-phase) as presented in FIG. 7. Each time point is an average of at least three biological replicates (±SD) with statistical comparisons (the stars *) were analyzed by the student's test (p≤0.05).
Figure 11B:
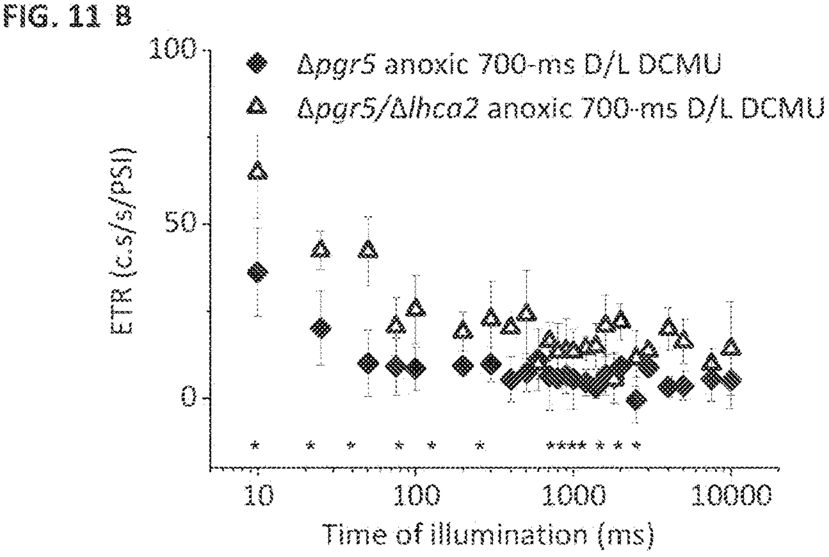

Example 4: Comparison of $H_2$ Production Under Replete Medium Conditions by the Single pgr5 Mutant and by the Double pgr5/lhca2 Mutant in a cc124 Genetic Background To assess $H_2$ production in pgr5 and pgr5/lhca2 production, $O_2$ and $H_2$ production as well as $CO_2$ uptake under ambient conditions were measured using mass inlet mass spectrometry (MIMS) (FIG. 9). Cells of pgr5/lhca2 and pgr5 mutant strains (back crossed into cc124/125) as well as WT cc124 were grown under photo-heterotrophic conditions, dark-adapted for 1 hour and shifted to a light intensity of 370 μmol photons $m^{-2}$ $s^{-1}$ for 16 min, followed by a strong light pulse of 2500 μmol photons $m^{-2}$ $s^{-1}$ for 2 min and another dark phase. In this experimental setup, $O_2$ evolution was observed in WT cc124 and in pgr5 after the onset of light but not in pgr5/lhca2 (FIG. 9A). During the strong light pulse, $O_2$ evolution was strongest in pgr5, followed by pgr5/lhca2 and WT cc124. On the other hand, $CO_2$ uptake started in the WT cc124 immediately after the onset of light and was boosted by the strong light pulse. In pgr5 only minor net $CO_2$ uptake was observed after the light was turned on (FIG. 9B); yet, upon the strong light pulse, $CO_2$ uptake is seen but to a lower extent as compared to WT. In pgr5/lhca2, the onset of light resulted in a $CO_2$ release, while the strong light pulse caused a miniscule $CO_2$ uptake in this strain. In contrast, $H_2$ production after light onset and light pulse was significantly higher in pgr5/lhca2 as compared to the two other strains (FIG. 9C). After 16 minutes, pgr5/lhca2 had accumulated more than 500 μM of $H_2$, while pgr5 and WT cc124 accumulated only about 80 and 10 μM of $H_2$, respectively (FIG. 9C). This revealed that under such particular conditions pgr5/lhca2 is indeed a potent $H_2$ producer. The accumulation of 500 μM of $H_2$ in 16 min, corresponds to 62.5 μmol $H_2$/mg Chl/h at 370 μmol photons $m^{-2}$ $s^{-1}$. The maximum theoretical efficiency of sunlight-to-$H_2$ conversion by wild-type algae is considered to be 13.4% (Torzillo et al., 2015. Crit Rev Biotechnol 35, 485-496). $H_2$ production rate needed to reach a 13.4% conversion efficiency is 413 μmol $H_2$ $mg^{-1}$ chl $h^{-1}$ at 8 h light per day (Torzillo et al., 2015, ibid; Toth and Yacoby, 2019. Trends Biotechnol. doi.org/10.1016/j.tibtech.2019.05.001). Thus, 62.5 μmol $H_2$ $mg^{-1}$ chl $h^{-1}$ at 370 μmol photons $m^{-2}$ $s^{-1}$, corresponds to theoretical efficiency of sunlight-to-$H_2$ conversion of more than 2%, when full sunlight of 2000 μmol photons $m^{-2}$ $s^{-1}$ is considered. The further increase of $H_2$ production in pgr5/lhca2 via an additional pulse of light at 2500 μmol photons $m^{-2}$ $s^{-1}$ supports the view that $H_2$ production at 370 μmol photons $m^{-2}$ $s^{-1}$ is not light-saturated. Millard et al. (Milrad Y et al., 2018. Plant Physiol 177, 918-926), revealed that in a 2 min MIMS experiment under conditions when Calvin cycle is not active, wild-type algae may produce up to 150 μmol $H_2$ $mg^{-1}$ chl $h^{-1}$ at 370 μmol $m^{-2}s^{-1}$, which drops steeply upon activation of $CO_2$ fixation. If these 150 μmol $H_2$ $mg^{-1}$ chl $h^{-1}$ at 370 μmol $m^{-2}s^{-1}$ are considered to be close to the theoretical efficiency of sunlight-to-$H_2$ conversion, pgr5/lhca2 possesses a sunlight-to-$H_2$ of more than 5. In pgr5/lhca2, a high rate of $H_2$ production could be maintained for 16 min, while net $CO_2$ fixation was absent, further supporting the view that Calvin Cycle is competitive to $H_2$ production as suggested (Milrad et al., 2018, ibid). The less efficient $CO_2$ fixation (FIG. 8) and high $O_2$ uptake as observed in pgr5 (Steinbeck et al., 2015. Front Plant Sci 6, 892), which is mirrored in pgr5/lhca2 as almost no $O_2$ evolution during the 370 μmol photons $m^{-2}$ $s^{-1}$ phase is observed, suggests that, despite similar photosynthetic electron transfer rates in pgr5/lhca2 as compared to WT (FIG. 10A, B), electrons are predominately transferred to hydrogenase or exploited for $O_2$ uptake in pgr5/lhca2, whereas in WT, more electrons are utilized for $CO_2$ fixation (FIG. 9). In pgr5, which has a pronounced respiration (Steinbeck et al., 2015, ibid), electrons could go predominantly into respiration, which would explain the missing $CO_2$ net fixation as $CO_2$ is released by mitochondria, despite strong $O_2$ evolution. Photosynthetic electron transfer rates (ETR) in WT and mutant strains were measured using electrochromic shift (ECS) signals with a Joliot-type spectrophotometer (JTS-10, Biologic; Bailleul, B., et al., 2010. ibid; FIGS. 10 and 11). Importantly, in pgr5/lhca2, in the presence of DCMU, ETR was significantly increased under oxic and anoxic conditions, denoting that the absence of LHCA2 seemed to rescue the ETR in the presence of DCMU in the pgr5 mutant (FIG. 11). This suggests that LHCA2 might act as a suppressor of PGR5 function in electron transfer regulation under conditions where PSII activity is blocked. Under anoxic conditions, $H_2$ production is expected and improved ETR capacity in the DCMU in pgr5/lhca2 versus pgr5, may explain higher $H_2$ production in pgr5/lhca2, as the more electrons were kept in the ETR chain in pgr5/lhca2, which apparently supports $H_2$ production. The same consideration could explain the higher $H_2$ production under ambient conditions.

Figure 7A:
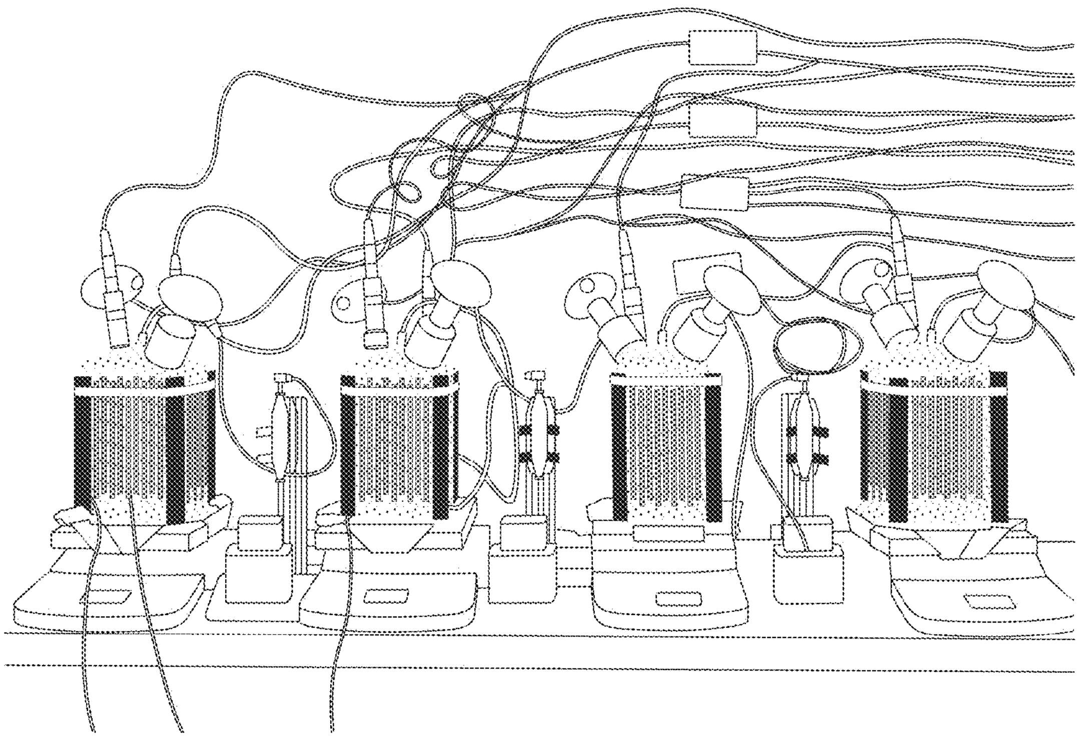
FIG. 7 shows an exemplary assembly of a system for producing hydrogen according to the teachings of the invention including several photo-bioreactors (PBRs, FIG. 7A) and a close-up of a portion of a single PBR (FIG. 7B) with $O_2$, $H_2$ and gas volume analyzers labelled.
Figure 7B:
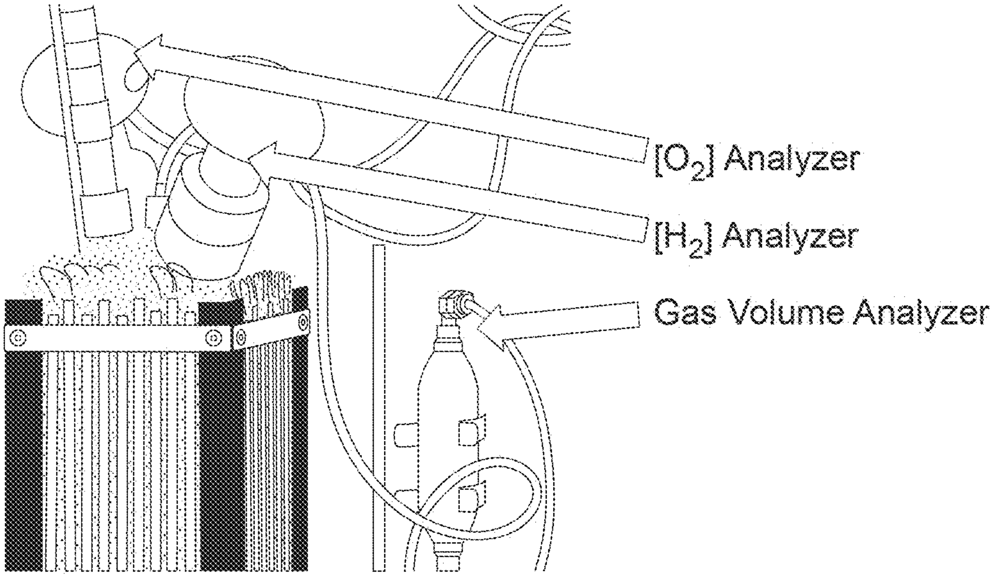

Example 5: Exemplary System for Producing $H_2$ by the Photosynthetic Microalgae of the Invention FIG. 7A is a photograph of 1 L PBR cultures of *Chlamydomonas* Elsa produced from *Chlamydomonas reinhardtii* by mutating the lhca2 and pgr5 genes. Cultures were grown at 5 μg chl/ml at a light intensity of 150 μmol $m^{-2}$×$s^{-1}$ in normal TAP medium. The headspace was sparged once, with nitrogen for 1 minute. Then, the PBR were kept in darkness for 2 hours after which irradiance was turned on. The bioreactors were continuously monitored for gas concentration using $H_2$ and $O_2$ detectors while gas accumulation was recorded using a Ritter's gas volume analyzer (Shown in FIG. 7B).

Example 6: Uneven Light/Dark Pulses Inhibit Oxygen Accumulation Under Extreme Irradiance Up to 10,000 μE (5 Times Full Sun Light)

Figure 8:
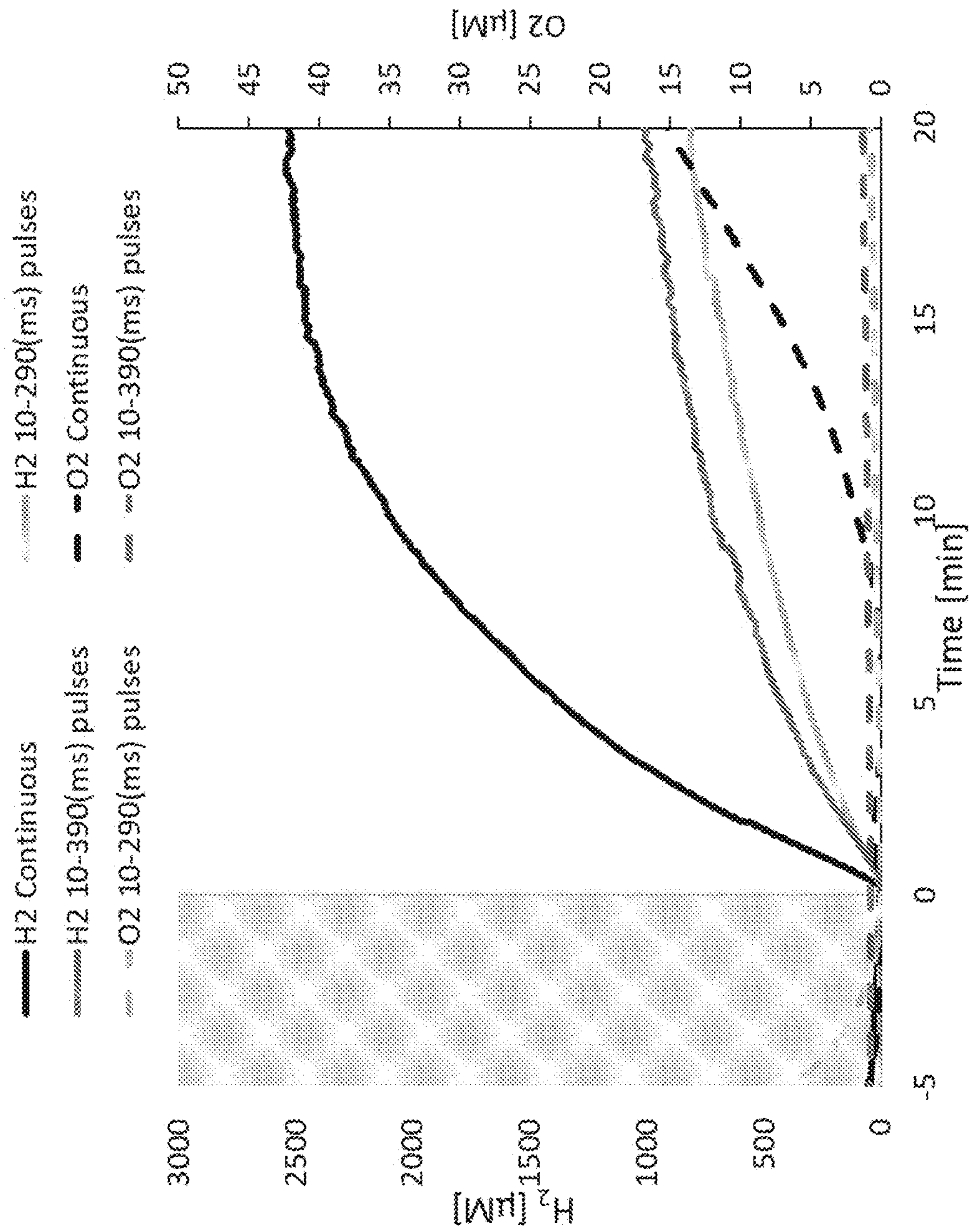
FIG. 8 shows $O_2$ and $H_2$ accumulation under different dark/light cycles in the milliseconds range as measured in a Membrane Inlet Mass Spectrometer under 10,000 HE.
Figure 9A:
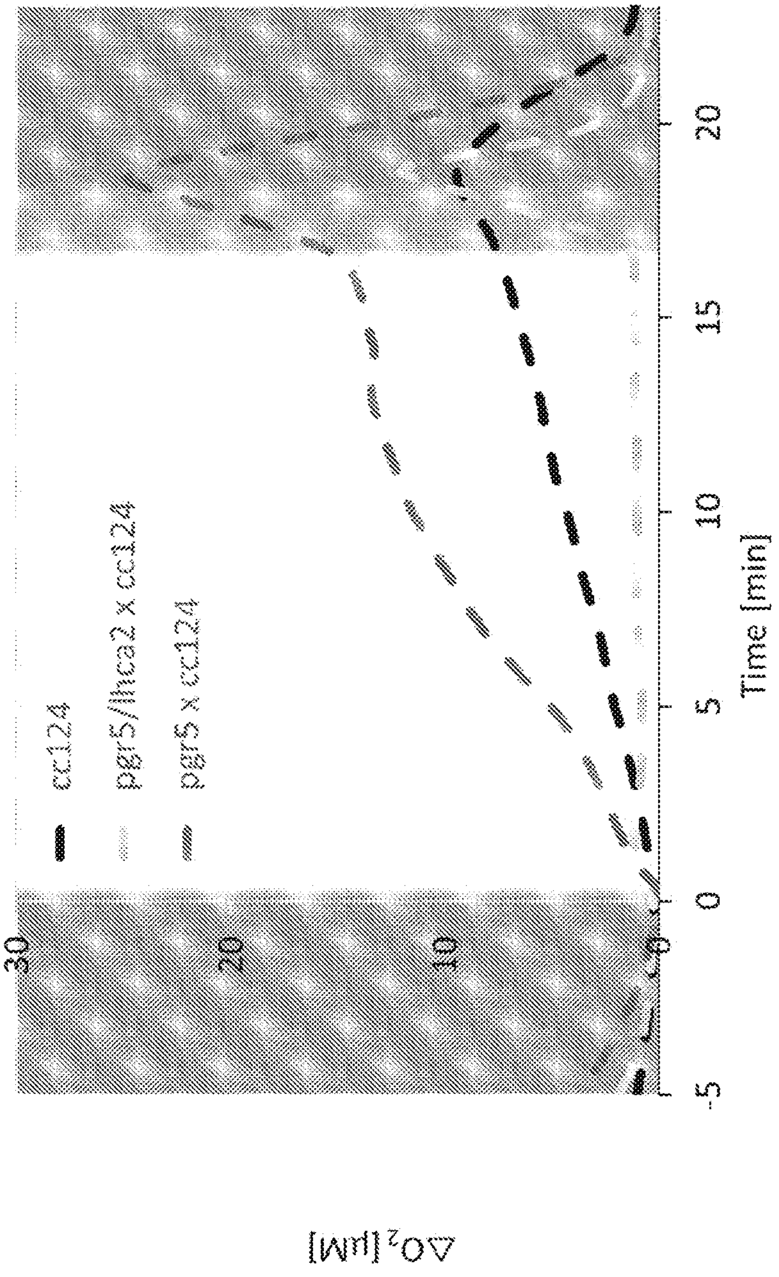
FIG. 9 shows short-term kinetics of dissolved, $O_2$, $CO_2$ and $H_2$ (A, B and C respectively) measured by MIMS. cc124, Δpgr5/Δlhca2, and Δpgr5 cells at a concentration of 15 mg Chl $L^{-1}$ were incubated in the dark for 2 hours, after which they were exposed to 16 min of illumination (370 μmol photons $m^{-2}$ $s^{-1}$; white background) followed by 2 min of high light (2500 μmol photons $m^{-2}$ $s^{-1}$; yellow background). (D) Absolute values of the $H_2$ (μmol) accumulated after 16 minutes of continuous illumination, magnified from C (dashed lines) for cc124, Δpgr5/Δlhca2, and Δpgr5 cells, shown as bars graph. Mean values and standard error bars are shown (n=3).
Figure 9B:
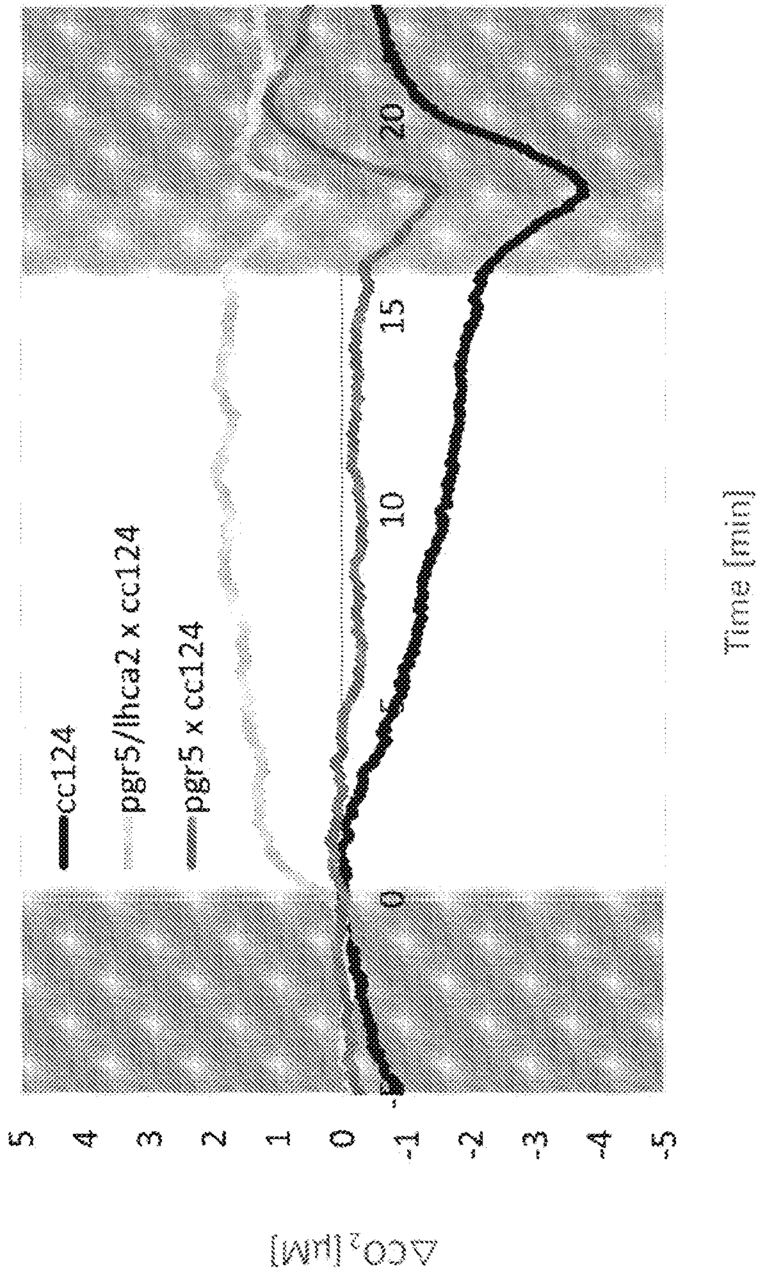
Figure 9C:
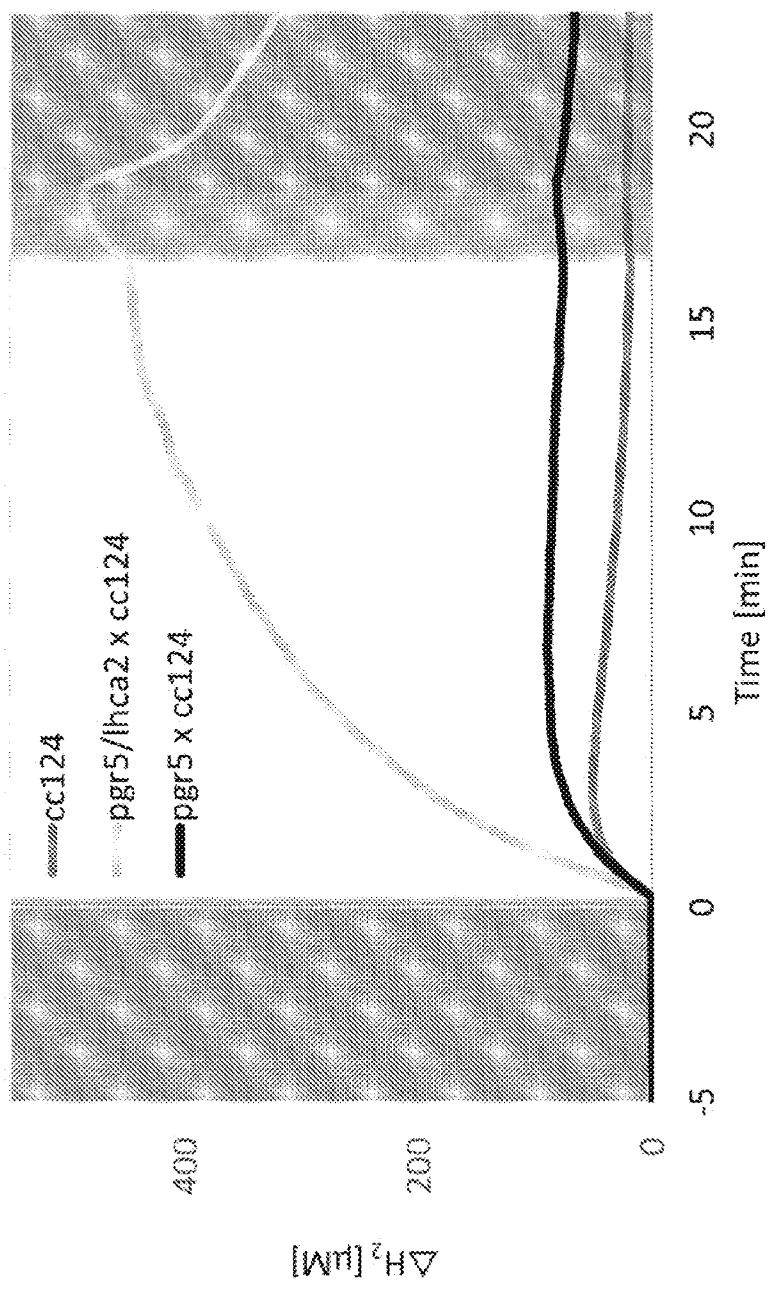
Figure 9D:
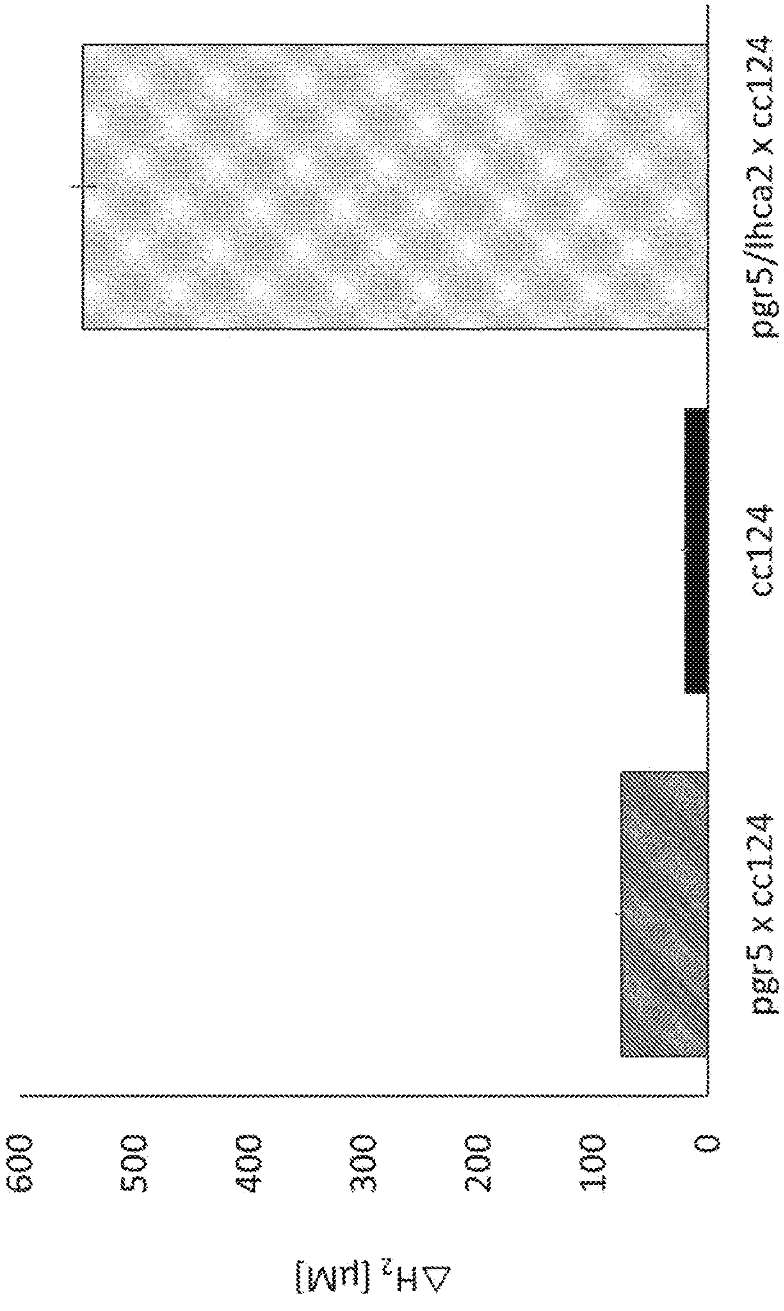
Figure 10A:
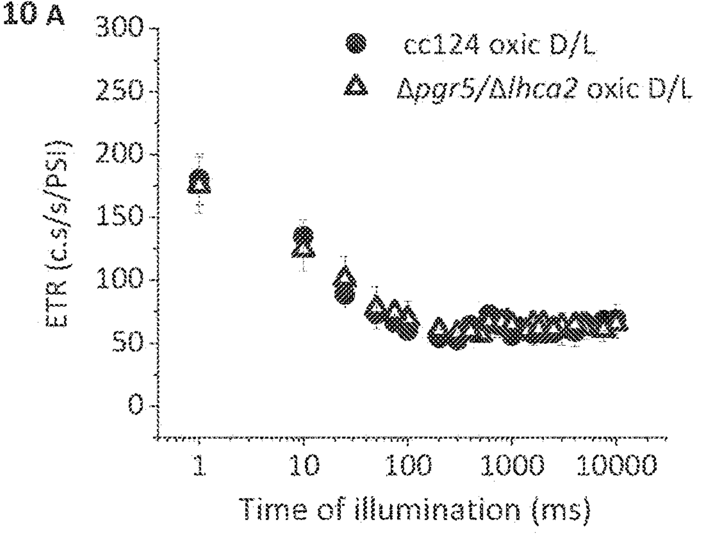
FIGS. 10A-10L show ETR measurement via DIRK after 20 min dark adaptation of the strains pgr5/lhca2, pgr5, lhca2 and WT cc124 during a first 10-s illumination period.
Figure 10B:
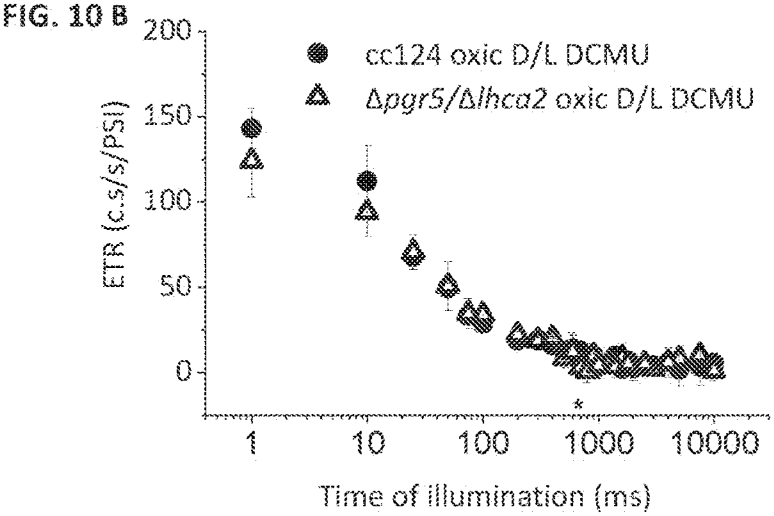
Figure 10C:
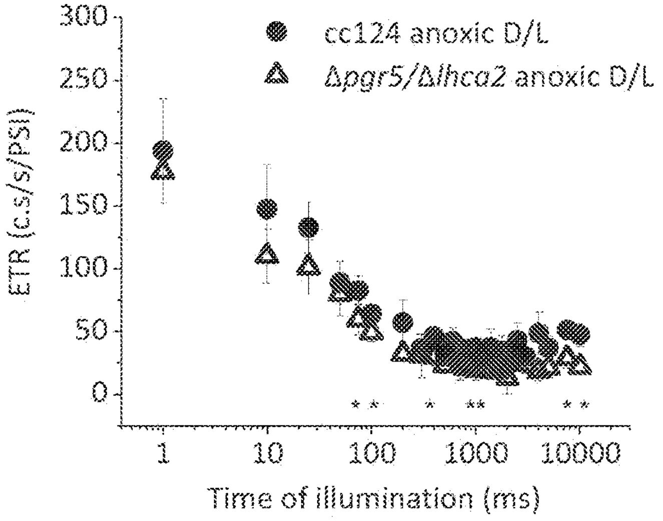
Figure 10D:
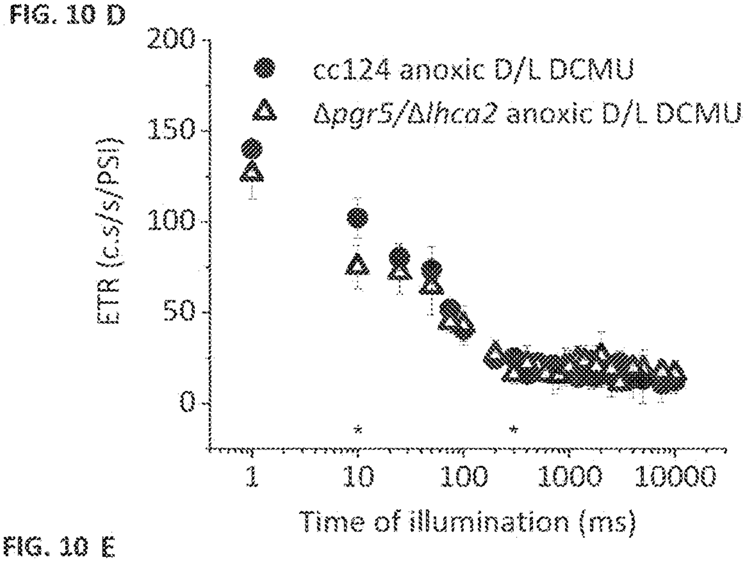
Figure 10E:
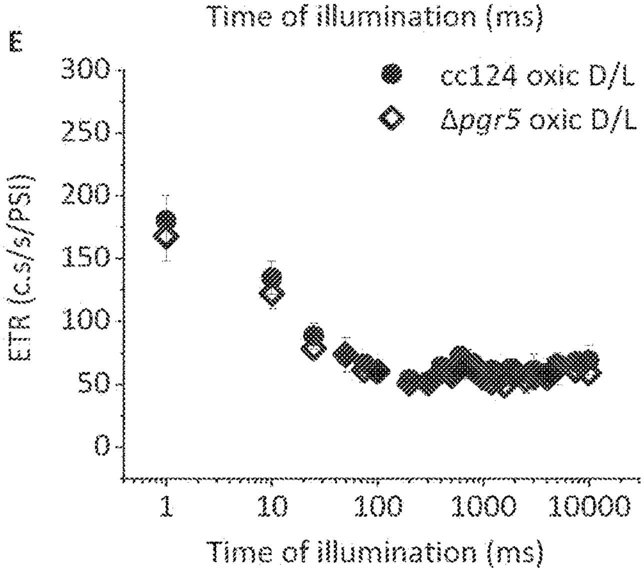
Figure 10F:
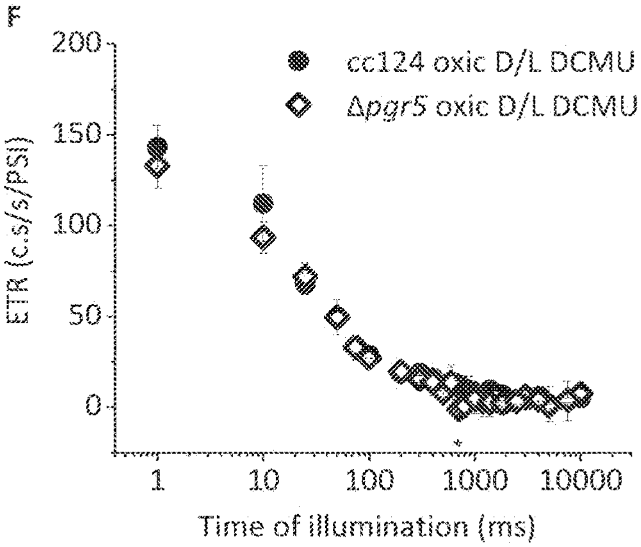
Figure 10G:
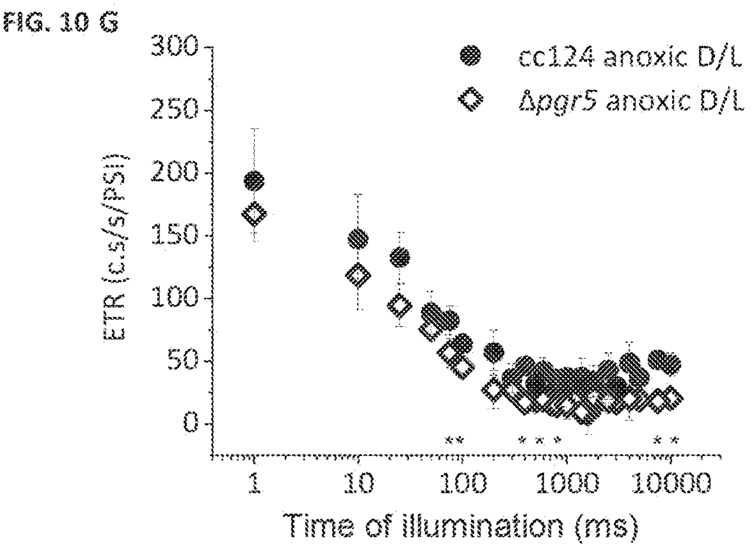
Figure 10H:
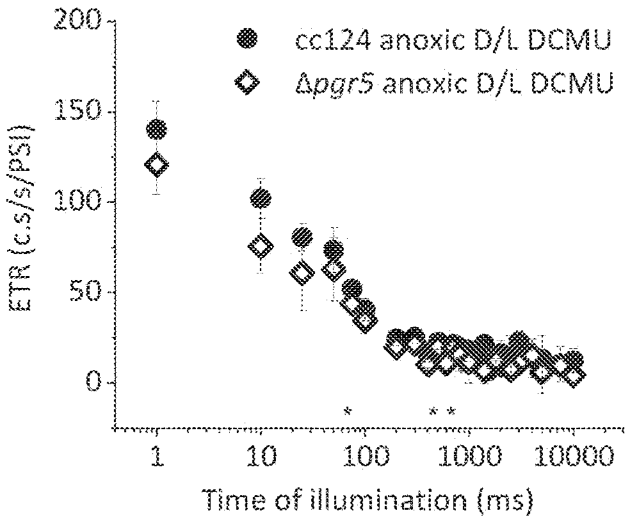
Figure 10I:
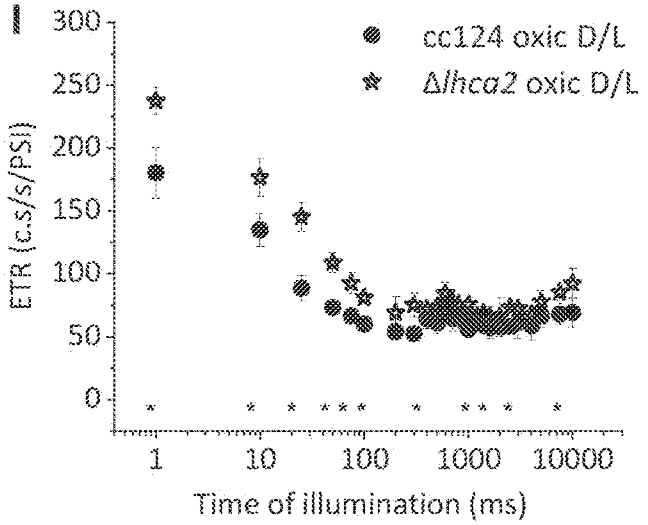
Figure 10J:
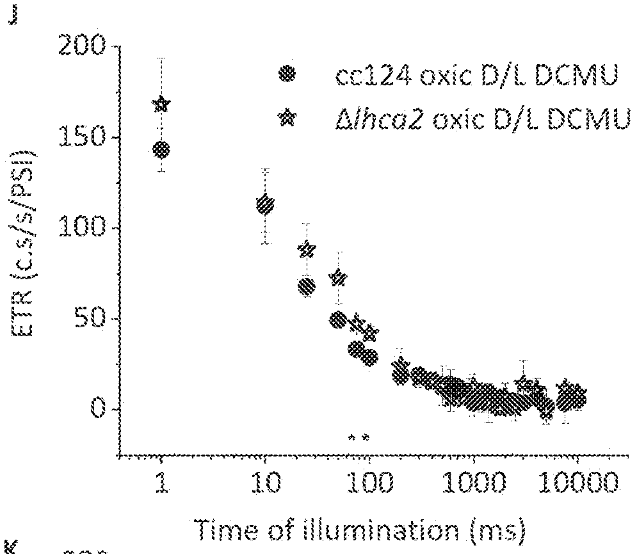
Figure 10K:
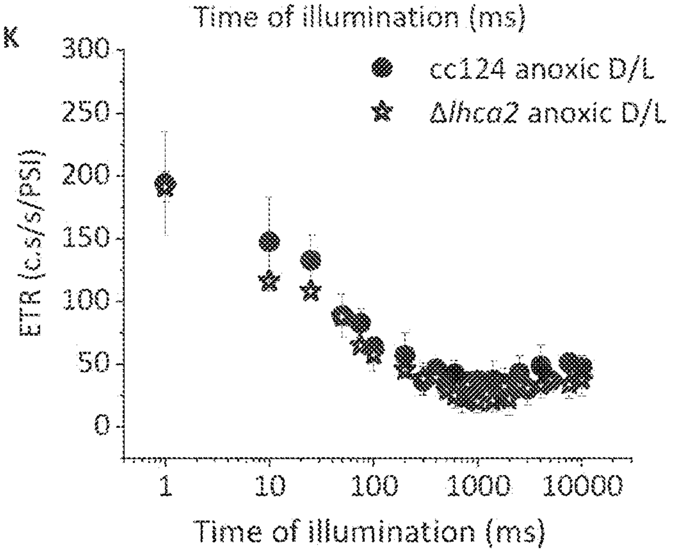
Figure 10L:
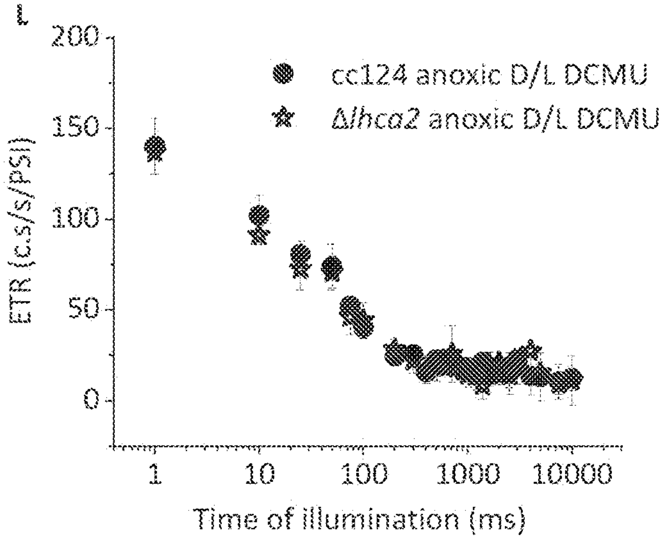

$H_2$ production by 5 ml of *C. elsa*, at a chlorophyl concentration of 10 mg per liter was measured under constant stirring within a measuring glass cuvette (FIG. 8). Irradiance was either constant, or uneven pulsed (10 ms light followed by 290 or 390 msec of darkness). Hydrogen and oxygen accumulation were measured simultaneously using a Membrane Inlet Mass Spectrometer. It can be seen that the uneven pulses methodology allows for continuous hydrogen production while totally inhibiting the accumulation of oxygen, thus allowing hydrogen production under an extreme light condition without compromising the integrity of the extremely oxygen sensitive hydrogenase enzyme.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A process for bio-production of hydrogen, the process comprising (i) culturing genetically modified photosynthetic microalgae selected from the group consisting of microalgae having reduced expression and/or activity of Proton Gradient Regulation 5 (PGR5) and microalgae having reduced expression and/or activity of PGR5 and Light Harvesting Complex Protein 2 (LHCA2) in a complete medium under ambient air and exposure to a single cycle of a dark period followed by exposure to light, wherein the light is at an intensity enabling photosynthesis; and (ii) collecting hydrogen produced by the genetically modified photosynthetic microalgae, wherein the genetically modified photosynthetic microalgae produce at least 10 μmole $H_2$ per mg chlorophyll of said microalgae per hour for at least 5 days.

2. The process of claim 1, wherein the dark period is from about 1 hour to about 10 hours.

3. The process of claim 1, wherein the photosynthetic light is selected from the group consisting of a continuous light at an intensity of from about 50 μE to about 600 μE and a pulsed light applied in cycles consisting of 1-20 msec of light followed by 100-500 msec of dark.

4. The process of claim 1, wherein the genetically modified photosynthetic microalgae are continuously grown in a single culture vessel.

5. The process of claim 1, wherein the LHCA2 comprises an amino acid sequence having at least 85% identity to the amino acid sequence set forth in SEQ ID NO: 1 and wherein the PGR5 comprises an amino acid sequence having at least 65% identity to the amino acid sequence set forth in SEQ ID NO: 3.

* * * * *

SEQUENCE LISTING

```
<160> NUMBER OF SEQ ID NOS: 4

<210> SEQ ID NO 1
<211> LENGTH: 245
<212> TYPE: PRT
<213> ORGANISM: Chlamydomonas

<400> SEQUENCE: 1

Met Ala Met Leu Leu Lys Ser Arg Val Ser Ala Gly Val Ser Arg Pro
1               5                   10                  15

Ser Arg Ala Thr Val Arg Val Ser Ala Ser Thr Arg Pro Met Trp Tyr
            20                  25                  30

Pro Gly Ala Thr Ala Pro Ala His Leu Asp Gly Ser Met Leu Gly Asp
        35                  40                  45

Tyr Gly Phe Asp Pro Leu Arg Leu Gly Val Asn Lys Asp Asn Leu Lys
    50                  55                  60

Trp Phe Arg Glu Ala Glu Leu Thr Asn Gly Arg Trp Ala Met Ala Ala
65                  70                  75                  80

Val Val Gly Ile Leu Phe Thr Asp Ala Val Gly Leu Pro Lys Phe Trp
                85                  90                  95

Thr Ala Gly Ala Glu Lys Tyr Ala Leu Asp Asn Gln Thr Leu Ala Leu
            100                 105                 110

Ile Glu Val Ala Val Phe Ala Val Leu Glu Gly Lys Arg Tyr Glu Ile
        115                 120                 125

Tyr Lys Lys Thr Gly Thr Gly Phe Leu Ser Phe Ala Pro Phe Asp Pro
    130                 135                 140

Met Gly Met Lys Ser Glu Glu Met Lys Leu Lys Glu Leu Lys Asn Gly
145                 150                 155                 160

Arg Leu Ala Met Leu Ala Phe Leu Gly Phe Cys Ser Gln Ala Ala Val
                165                 170                 175

Tyr Gly Lys Gly Pro Ile Glu Thr Leu Gln Leu His Leu Ala Asp Pro
            180                 185                 190

Gly His Asn Asn Ile Tyr Thr Ser Ser Val Gly Pro Glu Thr Ala Val
        195                 200                 205

Thr Val Ala Val Leu Cys Val Leu Pro Met Ile Ile Glu Ala Thr Lys
    210                 215                 220

Thr Leu Asn Pro Gly Lys Glu Ser Val Pro Tyr Phe Pro Trp Asn Glu
225                 230                 235                 240

Pro Trp Asn Lys Val
```

245

<210> SEQ ID NO 2
<211> LENGTH: 741
<212> TYPE: DNA
<213> ORGANISM: Chlamydomonas

<400> SEQUENCE: 2
atggccatgc tgctgaagtc ccgtgtgtcc gccggtgtgt cgcgcccctc gcgcgccacc 60
gtgcgcgtga gcgcgtcgac ccgccctatg tggtaccccg gcgccaccgc ccctgctcac 120
ctggacggct ccatgctggg tgactacggc ttcgaccccc tccgcctggg cgtgaacaag 180
gacaacctga agtggttccg tgaggctgag ctgaccaacg gccgctgggc catggctgcc 240
gttgtcggca tcctgttcac cgacgccgtg ggcctgccca agttctggac cgctggtgct 300
gagaagtacg ccctggacaa ccagaccctg gctctgatcg aggtcgccgt gttcgccgtg 360
ctggagggca agcgctacga gatctacaag aagaccggcg agaccggctt cctgtcgttc 420 gccccccttcg accccatggg catgaagagc gaggagatga agctgaagga gctgaagaac 480
ggccgcctgg ccatgctggc gttcctgggc ttctgctctc aggccgctgt gtacggcaag 540
ggccccattg agaccctgca gctgcacctg gctgaccccg gccacaacaa catctacacc 600
tcgtcggtgg gccctgagac cgccgtgacc gtggccgtgc tgtgcgtgct gcccatgatc 660
attgaggcca ccaagaccct gaaccccggc aaggagtccg tgccctactt cccctggaac 720
gagccctgga acaaggtgta a 741

<210> SEQ ID NO 3
<211> LENGTH: 141
<212> TYPE: PRT
<213> ORGANISM: Chlamydomonas

<400> SEQUENCE: 3

Met Leu Ala Ser Lys Pro Val Val Gly Val Arg Val Arg Ser Ser Thr
1 5 10 15

Ala Ser Thr Val Ala Arg Ala Asn Ile Arg Ser Leu Ala Val Ser Ser
20 25 30

Arg Val Ala Leu Ser Gly Gly Val Cys Gln Val Pro Thr Ser Val Val
35 40 45

Ala Pro Ala Pro Lys Ser Thr Gln Ser Thr Asn Ala Pro Arg Arg Lys
50 55 60

Pro Val Thr Met Met Gly Asn Lys Ala Thr Thr Gly Pro Phe Ala Pro
65 70 75 80

Leu Val Ile Val Val Arg Gly Ala Met Gly Glu Lys Pro Phe Asn Asn
85 90 95

Phe Arg Gly Lys Ala Ile Ser Tyr His Ser Gln Ile Ile Lys Asp Phe
100 105 110

Cys Lys Leu Leu Gly Val Asp Asn Lys Gln Val Gln Gly Val Ile Arg
115 120 125

Leu Ala Lys Lys Asn Gly Glu Lys Leu Gly Phe Leu Ala
130 135 140

<210> SEQ ID NO 4
<211> LENGTH: 426
<212> TYPE: DNA
<213> ORGANISM: Chlamydomonas

<400> SEQUENCE: 4

-continued

| | |
|---|---|
| atgctggcct ccaagcccgt tgttggcgtc cgcgtgcgca gctccaccgc ctcgacggtg | 60 |
| gctcgcgcca acatccgctc gctggcggtc tcctcgcgcg tggcgctgtc cggcggtgtg | 120 |
| tgccaggtgc cgacctcggt cgtcgcgccc gctcccaagt ccacccagtc taccaacgcg | 180 |
| ccccgccgca agcctgtgac gatgatgggc aacaaggcta ccactggccc cttcgcgcct | 240 |
| ctggtcatcg ttgttcgcgg tgccatgggc gagaagccat tcaacaactt ccgcggcaag | 300 |
| gccatctctt accactcgca gattatcaag gacttctgca agctgcttgg cgttgacaac | 360 |
| aagcaggtgc agggcgtcat ccgcctggcg aagaagaacg gcgagaagct gggcttcctg | 420 |
| gcttaa | 426 |